United States Patent

[19]

Boutherin-Falson et al.

[11] Patent Number: 5,981,544
[45] Date of Patent: Nov. 9, 1999

[54] MONO— OR DIKETONE TETRACYCLIC DERIVATIVES AND THERAPEUTICAL USES THEREOF

[75] Inventors: Odile Boutherin-Falson, Palaiseau; Stéphanie Desquand-Billiald, Paris; Anita Favrou, Cachan; Michel Finet, Chatenay Malabry; Olivier Tembo, Mery Sur Oise; Jean-Luc Torregrosa, Cachan; Sylvie Yannic-Arnoult, Epinay sur Orge; Cécile Joubert, Sceaux, all of France

[73] Assignee: Laboratoire Innothera, Arcueil, France

[21] Appl. No.: 09/077,435

[22] PCT Filed: Dec. 10, 1996

[86] PCT No.: PCT/FR96/01974

§ 371 Date: Sep. 21, 1998

§ 102(e) Date: Sep. 21, 1998

[87] PCT Pub. No.: WO97/21709

PCT Pub. Date: Jun. 19, 1997

[30] Foreign Application Priority Data

Dec. 12, 1995 [FR] France ................... 95 14684

[51] Int. Cl.⁶ ............... C07D 471/00; C07D 49/115; A61K 31/41; A61K 31/435
[52] U.S. Cl. .............. 514/285; 546/70; 568/328
[58] Field of Search .............. 540/70; 514/285; 568/328

[56] References Cited

U.S. PATENT DOCUMENTS 5,723,451  3/1998  Mjalli ................... 514/255

FOREIGN PATENT DOCUMENTS

92/19211  11/1992  WIPO .

OTHER PUBLICATIONS

CA 116:151679, 1991.
Chemical Abstracts 122:160618, 1994.
Chemical Abstracts 92:24218, 1979.
chemical Abstracts 92:58687, 1979.
Chemical Abstracts 124:232365, 1996.
Chemical Abstracts 96:162654, 1982.

*Primary Examiner*—D. Margaret M. Mach
*Attorney, Agent, or Firm*—Kenyon & Kenyon

[57] ABSTRACT

Invention concerning the therapeutic use of tetracyclic derivatives and their pharmaceutically acceptable salts having the following general formula:

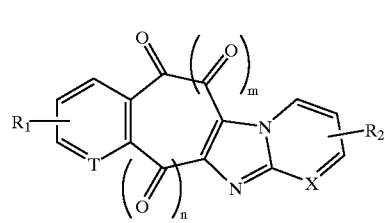

(I)

in which, independently of the other:

X is a carbon or nitrogen atom,

T is a carbon or nitrogen atom,

L is an oxygen atom or ketone functional protective group, $R_1$ is an atom of hydrogen, an atom of halogen, or a $C_1$ to $C_5$ alkyl radical, $R_2$ is a hydrogen atom, a halogen atom, a nitro radical, or a $C_1$ to $C_5$ alkyl radical, n and m are equal to 0 or to 1, but not independently of the other, so that if n is equal to 1, then m is equal to 0, and if n is equal to 0, then m is equal to 1.

49 Claims, No Drawings

MONO— OR DIKETONE TETRACYCLIC DERIVATIVES AND THERAPEUTICAL USES THEREOF

This application is a 371 of PCT/FR96/01974 filed December 1996.

The present invention concerns the use of tetracyclic derivatives and their pharmaceutically acceptable salts for obtaining a medication for the treatment of diseases involving an alteration in the venous function and/or inflammatory edema, and concerns the new compounds obtained. More particularly, it concerns derivatives of tetracyclic compounds comprising a structural group, 1,4-dihydro-1,4-dioxonaphthalene, one of the ketones of which may be protected. The invention concerns the therapeutic application of all these compounds.

The document, Chem. Rev., 63, 279–296 (1963) by M. F. Sartori describes the synthesis of heterocyclic quinones from 2,3-dichloro-1,4-dihydro-1,4-dioxonaphthalene, in particular, naphthoimidazopyridines, diones, and their derivatives.

The article, J. Amer. Chem. Soc. 79, 5708–5710 (1957) by P. Truitt, J. E. Cooper, and F. M. Wood, Jr. describes a controversial synthesis of 6,11-dihydro-6,11-dioxonaphtho [2',3':4,5]imidazo[1,2-a] pyridine, while the document, J. Org. Chem., 24, 374–380 (1959), by W. L. Mosby and R. J. Boyle evokes the theoretical possibility of obtaining three types of compounds of different structures: 5,6-dihydro-5, 6-dioxo-naphtho[1',2':4,5]imidazo[1,2-a]pyridine, 5,6-dihydro-5,6-dioxo-naphtho[1',2':4,5]-imidazo[2,3-a]pyridine, 6,11-dihydro-6,11-dioxo-naphtho-[2',3':4,5]imidazo[1,2-a]pyridine. The authors demonstrate the obtaining of the first type of structure. Concerning this same problem, the article J. Org Chem., 26, 1316–1318 (1961) by W. L. Mosby describes the possibility of obtaining two types of products with similar reactions: 5,6-dihydro-5,6-dioxo-naphtho[1',2':4,5]imidazo[1,2-a]pyridine (the so-called angular form) and 6,11-dihydro-6,11-dioxo-naphtho[2',3':4, 5]imidazo[1,2-a]pyridine (the so-called linear form). The authors note that the formation of the linear structure is obtained less readily than the angular structure. More drastic conditions are thus required for the formation of this structure (reflux at elevated temperature). The "angular" structure of the family is demonstrated in the synthesis of 5,6-dihydro-5,6-dioxo-naphtho[1',2':4,5]imidazo[1,2-a]pyridine using a specific reagent of orthodiketones in the paper in J. Org. Chem., 28, 1019–1022 (1963) by J. A. Van Allan and G. A. Reynolds.

U.S. Pat. No. 2,970,146, Jan. 31, 1961 (Cl. 260–256.4) by R. J. Boyle, O. G. Birsten, and W. L. Mosby describes the synthesis of new heterocyclic orthoquinones. The paper in Indian J. Chemistry 18B, 236–239 (1979) by N. R. Ayyanger, A. G. Lugade, and B. D. Tilak describes the univocal synthesis of 6,11-dihydro-6,11-dioxo-naphtho-[2', 3':4,5]imidazo[1,2'-a]pyridine.

The paper in J. Indian Chem. Soc. 68(9), 529–531 (1991) by A. S Yanni describes the synthesis and bactericidal and fungicidal activity of 6,11-dihydro-6,11-dioxo -pyrido[1', 2':1,2]imidazo[5,4-g]quinoline. Finally, German patent No. 1,108,699 by C. W. Schellhammer and G. Domagk describes the cytostatic and bacteriostatic activity of derivatives of 5,6-dihydro-5,6-dioxo-pyrido[1',2':1,2]imidazo[4,5-f] quinoline.

The tetracyclic derivatives and their pharmaceutically acceptable salts according to the present invention have the general formula:

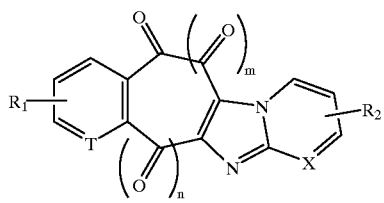

in which, independently of each other:
X is a carbon atom or a nitrogen atom,
T is a carbon atom or a nitrogen atom,
$R_1$ is a hydrogen atom; a halogen atom, or an alkyl radical of $C_1$ to $C_5$,
$R_2$ is a hydrogen atom, a halogen atom, a nitro radical, of an alkyl radical of $C_1$ to $C_5$,
n and m are equal either to 0 or 1, but not independently of each other, such that if n is equal to 1 then m is equal to 0 and if n is equal to 0 then m is equal to 1.

The invention also concerns the following new products:
5,6-dihydro-5,6-dioxo-9-methyl-naphtho-[1',2':4,5]imidazo [1,2-a]pyridine;
5,6-dihydro-5,6-dioxo-10-methyl-naphtho-[1',2':4,5] imidazo[1,2-a]pyridine;
5,6-dihydro-5,6-dioxo-11-methyl-naphtho-[1',2':4,5] imidazo[1,2-a]pyridine;
11-chloro-5,6-dihydro-5,6-dioxo-naphtho-[1',2':4,5]imidazo [1,2-a]pyridine;
5,6-dihydro-5,6-dioxo-9-fluoro-naphtho-[1',2':4,5]imidazo [1,2-a]pyridine;
9-chloro-5,6-dihydro-5,6-dioxo-4-nitro-naphtho-[1',2':4,5] imidazo[1,2-a]pyridine;
6,11-dihydro-6,11-dioxo-2-methyl-naphtho-[2',3':4,5] imidazo[1,2-a]pyridine;
2-chloro-6,11-dihydro-6,11-dioxo-naphtho-[2',3':4,5] imidazo[1,2-a]pyridine;
4-chloro-6,11-dihydro-6,11-dioxo-naphtho-[2',3':4,5] imidazo[1,2-a]pyridine;
6,11-dihydro-6,11-dioxo-2-fluoro-naphtho-[2',3':4,5] imidazo[1,2-a]pyridine.
2-chloro-6,11-dihydro-6,11-dioxo-7-nitro-naphtho-[2',3':4, 5]imidazo[1,2-a]pyridine
2-chloro-6,11-dihydro-6,11-dioxo-10-nitro-naphtho[2',3':4, 5]imidazo[1,2-a]pyridine
10-chloro-5,6-dihydro-5,6-dioxonaphtho-[1',2':4,5]imidazo [1,2-a]pyridine
4-chloro-5,6-dihydro-5,6-dioxonaphtho-[1',2':4,5]imidazo [1,2-a]pyridine
4-bromo-5,6-dihydro-5,6-dioxonaphtho-[1',2':4,5]-imidazo [1,2-a]pyridine
5,6-dihydro-5,6-dioxo-2-nitronaphtho[1',2':4,5]-imidazo[1, 2-a]pyridine
6,11-dihydro-6,11-dioxo-7-nitronaphtho-[2',3':4,5]imidazo [1,2-a]pyridine
6,11-dihydro-6,11-dioxo-10-nitronaphtho-[2',3':4,5]imidazo [1,2-a]pyridine
6,11-dihydro-6,11-dioxo-8-fluoronaphtho-[2',3':4,5]imidazo [1,2-a]pyridine
6,11-dihydro-6,11-dioxo-9-fluoronaphtho-[2',3':4,5]imidazo [1,2-a]pyridine
5,6-dihydro-5,6-dioxo-2-fluoronaphtho[1',2':4,5]-imidazo [1,2-a]pyridine
5,6-dihydro-5,6-dioxo-3-fluoronaphtho[1',2':4,5]-imidazo [1,2-a]pyridine
6,11-dihydro-6,11-dioxo-7-fluoronaphtho-[2',3':4,5]-imidazo[1,2-a]pyridine 6,11-dihydro-6,11-dioxo-10-fluoronaphtho-[2',3':4,5]
imidazo[1,2-a]pyridine
5,6-dihydro-5,6-dioxo-1-fluoronaphtho[1',2':4,5]-imidazo
[1,2-a]pyridine
5,6-dihydro-5,6-dioxo-4-fluoronaphtho[1',2':4,5]-imidazo
[1,2-a]pyridine
4,9-dichloro-5,6-dihydro-5,6-dioxonaphtho-[1',2':4,5]
imidazo[1,2-a]pyridine
6,11-dihydro-6,11-dioxo-7-fluoronaphtho-[2',3':4,5]imidazo
[1,2-a]pyridine
6,11-dihydro-6,11-dioxo-10-fluoronaphtho-[2',3':4,5]
imidazo[1,2-a]pyridine
5,6-dihydro-5,6-dioxo-1-methyl-naphtho[1',2':4,5]-imidazo
[1,2-a]pyridine
5,6-dihydro-5,6—dioxo-4-methyl-naphtho[1',2':4,5]-
imidazo[1,2-a]pyridine
9-chloro-6,11-dihydro-6,11-dioxo-7-methylnaphtho-[2',
3':4,]imidazo[1,2-]pyridine
9-chloro-6,11-dihydro-6,11-dioxo-10-methyl-naphtho[2',
3':4,]imidazo[1,2-a]pyridine
9-chloro-5,6-dihydro-5,6-dioxo-1-methylnaphtho-[1',2':4,]
imidazo[1,2-a]pyridine
9-chloro-5,6-dihydro-5,6-dioxo-4-methylnaphtho-[1',2':4,5]
imidazo[1,2-a]pyridine
6,11-dihydro-6,11-dioxo-8-methylnaphtho-[2',3':4,5]-
imidazo[1,2-a]pyridine
6,11-dihydro-6,11-dioxo-9-methylnaphtho-[2',3':4,5]-
imidazo[1,2-a]pyridine
5,6-dihydro-5,6-dioxo-2-methylnaphtho-[1',2':4,5]-imidazo
[1,2-a]pyridine
5,6-dihydro-5,6-dioxo-3-methylnaphtho-[1',2':4,5]-imidazo
[1,2-a]pyridine The invention also concerns the following intermediate products:
2,3-dibromo-1,4-dihydro-1,4-dioxo-6-fluoro-naphthalene
2,3-dibromo-1,4-dihydro-1,4-dioxo-5-fluoro-naphthalene
2,3-dibromo-1,4-dihydro-1,4-dioxo-5-methyl-naphthalene The invention also concerns the use of tetracyclic derivatives and their pharmaceutically acceptable salts having the general formula (I) above for obtaining a specific medication:

for the treatment of functional and organic venous insufficiency;
for the treatment of hemorrhoidal pathologies;
for the treatment of migraine;
for the treatment of osteoarticular, dermatological and cardiovascular inflammations;
for the treatment of states of shock involving a substantial drop in arterial pressure, more particularly in states of septic shock.

Specifically, the compounds of the present invention have the general formula (I) illustrated below:

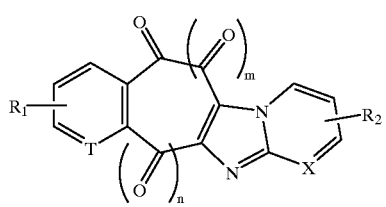

(I)

where: n=0 or 1; m=0 or 1; T=C, N; X=C, N;
R₁=H, CH₃, Cl, Br, F;
R₂=H, NO₂, Cl, Br, F, CH₃

The present invention also concerns the salts of salifiable compounds of formula (I). These salts include the addition salts of inorganic acids such as hydrochloric, hydrobromic, sulfuric, phosphoric, or nitric acids, as well as the addition salts of organic acids such as acetic, propionic, oxalic, citric, maleic, fumaric, succinic, and tartaric acids.

The invention is illustrated by the following nonlimiting examples.

The examples indicated by a number correspond to new compounds, while the examples involving a letter correspond to known compounds.

In all the examples, the analyses are conducted as indicated below:

Melting points: They are obtained on an apparatus of the "Banc de Kofler type—LEICA—REICHERT, model WME.

Thin-layer chromatography: They were obtained on plates of silica gel with fluorescence indicator $UV_{254}$, 0.25 mm in thickness, of the MACHEREY-NAGEL type (Reference 805 023). The elution solvents are indicated for each compound.

Mass spectra: They were produced either on a spectrometer of the AEI MS-50 type or on a spectrometer of the FISONS VG PLATFORM type. The mode of ionization is indicated for each analysis.

NMR spectra: The NMR spectra of $^1H$ and $^{13}C$ were obtained either on a spectrometer of the JEOL type, respectively at 270 MHz and at 68 MHz, or on a spectrometer of the BRUCKER type, respectively at 400 MHz and at 100 MHz. The deuterated solvents used are indicated for each analysis.

Infrared spectra: They were obtained on a spectrometer of the Nicolet 205 FT-IR type. They were produced at 1% (m/m) in a dispersion in KBr.

EXAMPLE 1

5,6-Dihydro-5,6-dioxo-9-methyl-naphtho[1',2':4,5]-imidazo[1,2-a]pyridine 4.76 g (44 mmol) of 2-amino-5-methylpyridine in solution in 50 mL of ethanol are added to a suspension of 10 g (44 mmol) of 2,3-dichloro-1,4-dihydro-1,4-dioxonaphthalene in 150 mL of ethanol, which is brought to reflux. After 48 h of reflux, the reaction mixture is evaporated to dryness and purified on a flash column (support: silica; conditioning: heptane; eluent: dichloromethane) to produce 5 g of 5,6-dihydro-5,6-dioxo-9-methyl-naphtho[1',2':4,5]-imidazo[1,2-a]pyridine sulfate in the form of orange crystals.

Yield: 48%
Melting point: >260° C.
Rf: 0.54 ($CH_2Cl_2$/methanol, 98/2)
MS (I.E.): m/z 262 (M+.)
$^1$H-NMR (CDCl₃): δ (ppm) 9.11 (s, 1H, H-8) 8.13 (m, 2H, H-1, H-4) 7.68 (2m, 2H, H-2, H-3) 7.50 (m, 2H, H-10, H-11) 2.47 (s, 3H, CH₃)
$^{13}$C-NMR(CDCl₃): (ppm) 182.16, 167.14 (2C, Cquat) 153.85, 149.24 (2C, Cquat) 135.24, 134.95 (2C, C-2, C-3) 131.58 (1C, Cquat) 130.57 (2C, C-10, Cquat) 130.00, 124.48 (2C, C-1, C-4) 127.25 (1C, C-8) 120.40 (1C, Cquat) 117.39 (1C, C-11) 18.25 (1C, CH₃)
IR (KBr): μ ($cm^{-1}$) 1689, 1652 (C=O)

EXAMPLE 2

5,6-Dihydro-5,6-dioxo-10-methyl-naphtho[1',2':4,5]-imidazo[1,2-a] pyridine 2.16 g (20 mmol) of 2-amino-4-methylpyridine in solution in 50 mL of ethanol are added to a suspension of 4.54 g (20 mmol) of 2,3-dichloro-1,4-dihydro-1,4-dioxonaphthalene in 200 mL of ethanol that is brought to reflux. After 18 h of reflux, the reaction mixture is evaporated to dryness and purified on a flash column (support: silica; conditioning: heptane; eluent: dichloromethane) to produce 3.19 g of 5,6-dihydro-5,6-dihydro-5,6-dioxo-10-methyl-naphtho[1',2':4,5]imidazo[1,2-a]pyridine.

Yield: 61%
Melting point: >260° C.
Rf: 0.64 ($CH_2Cl_2$/Methanol, 97/3)
MS (I.E.): m/z 262 (M+.)
$^1$H-NMR ($CDCl_3$): (ppm) 9.11 (d, 1H, H-8, $J_{H8-H9}$=6.71 Hz) 8.08 (m, 2H, H-1, H-4) 7.65, 7.53 (2m, 2H, H-2, H-3) 7.48 (m, 1H, H-11) 7.02 (d, 1H, H-9, $J_{H8-H9}$=6.71 Hz) 2.52 (s, 3H, $CH_3$)
$^{13}$C-NMR ($CDCl_3$): (ppm) 182.39, 167.26 (2C, Cquat) 153.20, 150.79 (2C, Cquat) 144.48 (1C, Cquat) 135.22, 130.68 (2C, C-2, C-3) 131.51 (1C, Cquat) 130.02, 124.63 (3C, C-1, C-4, Cquat) 128.18 (1C, C-8) 120.01 (1C, Cquat) 118.99 (1C, C-11) 117.15 (1C, C-9) 22.00 (1C, $CH_3$)
IR (KBr): $\mu$ ($cm^{-1}$) 1701, 1656 (C=O)

EXAMPLE 3
5,6-Dihydro-5,6-dioxo-11-methyl-naphtho[1',2':4,5]-imidazo[1,2-a] pyridine 4.76 g (44 mmol) of 2-amino-3-methylpyridine in solution in 50 mL of ethanol are added to a suspension of 10 g (44 mmol) of 2,3-dichloro-1,4-dihydro-1,4-dioxonaphthalene in 150 mL of ethanol that is brought to reflux. After 48 h of reflux, the reaction mixture is evaporated to dryness and purified on a flash column (support: silica; conditioning: heptane; eluent: dichloromethane) to produce 6 g of 5,6-dihydro-5,6-dioxo-11-methyl-naphtho[1',2':4,5]imidazo[1,2-a]pyridine in the form of orange crystals.

Yield: 52%
Melting point: >260° C.
Rf: 0.46 ($CH_2Cl_2$/Methanol, 99/1)
MS (I.E.): m/z 262 (M+.)
$^1$H-NMR ($CDCl_3$): (ppm) 9.16 (d, 1H, H-8, $J_{H8-H9}$=6.72 Hz) 8.23 (d, 1H, H-1, $J_{H1-H2}$=7.63 Hz) 8.11 (d, 1H, H-4, $J_{H3-H4}$=7.63 Hz) 7.69 (dd, 1H, H-3, $J_{H3-H4}$=$J_{H2-H3}$=7.63 Hz) 7.50 (dd, 1H, H-2, $J_{H2-H3}$=$J_{H1-H2}$=7063 HZ) 7.43 (d, 1H, H-10, $J_{H9-H10}$=7.32 Hz) 7.09 (dd, 1H, H-9, $J_{H8-H9}$=$J_{H9-H10}$=6.72 Hz) 2.72 (s, 3H, $CH_3$)
$^{13}$C-NMR ($CDCl_3$): (ppm) 182.29 (1C, C-5) 167.32 (1C, C-6a) 153.61 (1C, C-12a) 150.56 (1C, C-11a) 135.18 (1C, C-2) 131.73 (1C, C-4a) 131.32 (1C, C-10) 130.82 (1C, C-12b) 130.55 (1C, C-3) 130.00 (1C, C-4) 128.73 (1C, Cquat) 126.72 (1C, C-8) 124.75 (1C, C-1) 116.65 (1C, C-9) 16.87 (1C, $CH_3$)
IR (KBr): $\mu$ ($cm^{-1}$) 1691, 1646 (C=O)

EXAMPLE 4
11-Chloro-5,6-dihydro-5,6-dioxo-naphtho[1',2':4,5]-imidazo[1,2-a] pyridine 2.00 g (15.56 mmol) of 2-amino-3-chloropyridine are added to a suspension of 2.86 g (10.3 mmol) of 1,2-dihydro-1,2-dioxo-4-sulfonate of potassium naphthalene in 50 mL of distilled water. This mixture is brought to reflux for 4 h and 30 min. After complete cooling, the precipitate is filtered on fritted glass, washed with distilled water, and dried. The light brown solid obtained is purified on a flash column (support: silica; eluent: dichloromethane/ethyl acetate, 100/0 to 96/4) to produce 0.63 g of 11-chloro-5,6-dihydro-5,6-dioxo-naphtho[1',2':4,5] imidazo[1,2-a]pyridine.

Yield: 21%
Rf: 0.37 ($CH_2Cl_2$/ethyl acetate, 96/4)
MS (I.E.): m/z 282, 284 (M+.)
$^1$H-NMR ($CDCl_3$): (ppm) 9.25 (d, 1H, H-8, $J_{H8-H9}$=6.71 Hz) 8.33 (d, 1H, H-1, $J_{H1-H2}$=7.33 Hz) 8.15 (dd, 1H, H-4, $J_{H3-H4}$=7.94 Hz) 7.70 (m, 2H, H-10, H-3) 7.54 (t, 1H, H-2, $J_{H2-H3}$=$J_{H1-H2}$7.56 Hz) 7.14 (t, 1H, H-9, $J_{H8-H9}$=$J_{H9-H10}$= 6.91 Hz)
$^{13}$C-NMR ($CDCl_3$): (ppm) 135.50 (1C, C-2) 131.08 (1C, C-10) 130.95 (1C, C-3) 130.33 (1C, C-4) 127.40 (1C, C-8) 125.32 (1C, C-1) 124.61 (1C, C-11) 116.35 (1C, C-9)
IR (KBr): $\mu$ ($cm^{-1}$) 1653 (C=O)

EXAMPLE 5
5,6-Dihydro-5,6-dioxo-5-fluoro-naphtho[1',2':4,5]imidazo [1,2-a] pyridine 0.635 g (5.7 mmol) of 2-amino-5-fluoropyridine is added to a suspension of 1.200 g (4.3 mmol) of 1,2-dihydro-1,2-dioxo-4-sulfonate of potassium naphthalene in 40 mL of water. The reaction mixture is heated to reflux for 3 h. After complete cooling, the precipitate formed is filtered on fritted glass, washed with water and dried. The red solid obtained is purified on a flash column (support: silica; eluent: dichloromethane/ethyl acetate, 100/0 to 90/10) to produce 0.023 g of 5,6-dihydro-5,6-dioxo-9-fluoro-naphtho[1',2':4,5]imidazo[1,2-a]pyridine in the form of yellow crystals after decoloration with animal black.

Yield: 2%
Rf: 0.42 ($CH_2Cl_2$/ethyl acetate, 90/10)
MS (I.E.): m/z 266 (M+.)
$^1$H-NMR (270 MHz, $CDCl_3$): d (ppm) 9.27 (m, 1H, H-8, $J_{H8-F}$=4.88 Hz) 8.17, 8.15 (2d, 2H, H-1, H-4, $J_{H1-H2}$=$J_{H3-H4}$=7.32 Hz) 7.80 (dd, 1H, H-10, $J_{H10-H11}$=9.77 Hz, $J_{H10-F}$=4.88 Hz) 7.71 (t, 1H, H-2, $J_{H1-H2}$=$J_{H2-H3}$=7.63 Hz 7.53 (m, 2H, H-3, H-11)
IR (KBr): $\mu$ ($cm^{-1}$) 1686, 1654, 1633 (C=O)

EXAMPLES 6 and 7
2-Chloro-6,11-dihydro-6,11-dioxo-7-nitronaphtho[2',3':4,5] imidazo [1,2-a]pyridine or 2-Chloro-6,11-dihydro-6,11-dioxo-10-nitronaphtho[2',3':4,5]imidazo [1,2-a]pyridine and 9-Chloro-5,6-dihydro-5,6-dioxo-4-nitronaphtho[1',2':4,5] imidazo [1,2-a]pyridine 2.50 g (19.0 mmol) of 2-amino-5-chloropyridine are added to a solution of 2.50 g (11.0 mmol) of 2,3-dichloro-1,4-dihydro-1,4-dioxo-5-nitronaphthalene in 500 mL of ethanol. This mixture is heated to reflux for 62 h and 50 min. The solution passes from yellow to claret-colored, then to orange. After cooling, the reaction mixture is filtered. The precipitate is washed with ethanol, then dried in an oven for 20 h. The precipitate obtained is recrystallized in 650 mL of ethanol. This precipitate is purified on a flash column (support: silica; eluent: dichloromethane). 0.260 g of 2-chloro-6,11-dihydro-6,11-dioxo-7-nitronaphtho[2',3':4,5] imidazo[1,2-a]-pyridine or 2-chloro-6,11-dihydro-6,11-dioxo-10-nitronaphtho[2',3':4,5]imidazo[1,2-a] pyridine is obtained in the form of orange crystals, and 0.495 g of 10-chloro-5,6-dihydro-5,6-dioxo-4-nitronaphtho[1',2':4,5] imidazo[1,2-a]pyridine is formed in the form of orange crystals.

2-Chloro-6,11-dihydro-6,11-dioxo-7-nitronaphtho[2',3':4,5] imidazo [1,2-a]pyridine or 2-Chloro-6,11-dihydro-6,11-dioxo-10-nitronaphtho[2',3':4,5]imidazo [1,2-a] [pyridine]

Yield: 9%
Melting point: >260° C.
Rf: 0.75 ($CH_2Cl_2$/MeOH, 93/2)
MS (I.E.): 327, 329 (M$^{+.}$)
$^1$H-NMR ($CD_2Cl_2$): δ (ppm) 9.38 (dd, 1H, H-1, $J_{H1-H3}$= 1.66 Hz, $J_{H1-H4}$=0.83 Hz) 8.30 (dd, 1H, H-10 or H-7, $J_{H9-H10}$ or $J_{H7-H8}$=7.05 or 7.47 Hz, $J_{H8-H10}$ or $J_{H7-H9}$=2.08 or 1.66 Hz) 7.82 (dd, 1H, H-4, $J_{H3-H4}$=9.55 Hz or $J_{H1-H4}$=0.83 Hz) 7.60(m, 3H, H-3, H-8 et H-9)

IR (KBr): ν (cm$^{-1}$) 1650 (C=O), 1540, 1400 (NO$_2$)

9-Chloro-5,6-dihydro-5,6-dioxo-4-nitronaphtho[1',2':4,5]imidazo [1,2-a]pyridine

Yield: 13%
Melting point: >260° C.
Rf: 0.35 (CH$_2$Cl$_2$/MeOH, 98/2)
MS (I.E.): 327, 329 (M+.)
$^1$H-NMR (CD$_2$Cl$_2$): δ (ppm) 9.30 (dd, 1H, H-8, $J_{H8-H10}$=2.16 Hz, $J_{H8-H11}$=0.83 Hz) 8.40 (dd, 1H, H-1, $J_{H1-H2}$=7.89 Hz, $J_{H1-H3}$=1.25 Hz) 7.86 (t, 1H, H-2, $J_{H2-H3}J_{H1-H2}$=7.89 Hz) 7.82 (dd, 1H, H-11, $J_{H10-H11}$=9.55 Hz, $J_{H8-H11}$=0.83 Hz) 7.68 (dd, 1H, H-10, $J_{H10-H11}$=9.55 Hz or $J_{H8-H10}$=2.16 Hz) 7.52 (dd, 1H, H-3, $J_{H2-H3}$=7.89 Hz or $J_{H1-H3}$=1.25 Hz)
$^{13}$C-NMR (CD$_2$Cl$_2$): δ (ppm) 166.94 (1C, Cquat) 136.87 (1C, C-2) 134.26 (1C, C-1) 127.58 (1C, C-3) 119.26 (1C, C-11)
IR (KBr): ν (cm$^{-1}$) 1650 (C=O), 1540(NO$_2$)

EXAMPLE 8

6,11-Dihydro-6,11-dioxo-2-methyl-naphtho[2',3':4,5]imidazo[1,2-a] pyridine 0.55 g (5.08 mmol) of 2-amino-5-methylpyridine is added to a suspension of 0.45 g (2.16 mmol) of 3-chloro-1,4-dihydro-1,4-dioxo-2-hydroxynaphthalene in 15 mL of 1,2-dimethoxyethane. The reaction medium is brought to reflux for 21 h. After complete cooling, it is diluted with 120 mL of dichloromethane. The organic phase is washed successively with a saturated solution of sodium hydrogen carbonate and sodium chloride, then dried on sodium sulfate and evaporated under reduced pressure. The raw product obtained is purified on a medium-pressure column (support: silica; eluent: dichloromethane/heptane/ethyl acetate, 68/40/2) to produce 0.096 g of 6,11-dihydro-6,11-dioxo-2-methyl-naphtho[2',3':4,5]imidazo[1,2-a]pyridine in the form of yellow crystals after decoloration with animal black.

Yield: 17%
Rf: 0.34 (CH$_2$Cl$_2$/ethyl acetate, 94/6)
MS (I.E.): m/z 262 (M+.)
$^1$H-NMR (CD$_2$Cl$_2$): (ppm) 9.21 (s, 1H, H-1) 8.22 (m, 2H, H-7, H-10) 7.78 (m, 3H, H-4, H-8, H-9) 7.49 (dd, 1H, H-3, $J_{H3-H4}$=9.16 Hz, $J_{H1-H3}$=1.52 Hz) 2.48 (s, 3H, CH$_3$)
IR (KBr): ν (cm$^{-1}$) 1685 (C=O)

EXAMPLE 9

2-Chloro-6,11-dihydro-6,11-dioxo-naphtho[2',3':4,5]imidazo[1,2-a] pyridine 1.58 g (12.30 mmol) of 2-amino-5-chloropyridine are added to a suspension of 1.29 g (6.21 mmol) of 3-chloro-1,4-dihydro-1,4-dioxo-2-hydroxynaphthalene in solution in 10 mL of 1,2-dimethoxyethane. The reaction medium is brought to reflux for 23 h. After complete cooling, the medium is diluted in 10 mL of water. The precipitate is filtered, washed with water and heptane, and dried. The precipitate is then diluted in dichloromethane and the organic phase is washed successively with a saturated solution of sodium hydrogen carbonate and sodium chloride. The organic phase is dried on sodium sulfate, filtered, and evaporated under reduced pressure. The raw product obtained is purified on a flash column (support: silica; eluent: dichoromethane/heptane/methanol, 79.5/20.0/0.5) to produce 0.07 g of 2-chloro-6,11-dihydro-6,11-dioxo-naphtho[2',3':4,5]imidazo [1,2-a]pyridine in the form of yellow crystals after decoloration with animal black.

Yield: 4%
Melting point: >300° C.
Rf: 0.27 (CH$_2$Cl$_2$/ethyl acetate, 96/4)
MS (I.E.): m/z 282 (M+.)
$^1$H-NMR (CD$_2$Cl$_2$): (ppm) 9.49 (d, 1H, H-1, $J_{H1-H3}$=2.13 Hz) 8.25 (m, 2H, H-7, H-10) 7.87 (d, 1H, H-4, $J_{H3-H4}$=9.77 Hz) 7.79 (m, 2H, H-8, H-9) 7.61 (dd, 1H, H-3, $J_{H3-H4}$=9.76 Hz, $J_{H1-H3}$=2.13 Hz)
$^{13}$C-NMR (CD$_2$Cl$_2$): (ppm) 183.08 (1C, C=O) 178.13 (1C, C=O) 162.73, 160.86 (2C, Cquat) 149.26, 148.08, 146.75 (3C, Cquat) 134.59, 134.30 (2C, C-8, C-9) 132.53 (1C, C-3) 130.40 (1C, C-2) 127.70, 126.85 (2C, C-7, C-10) 126.73 (1C, C-1) 120.24 (1C, C-4)
IR (KBr): ν (cm$^{-1}$) 1686, 1651 (C=O)

EXAMPLE 10

4-Chloro-6,11-dihydro-6,11-dioxo-naphtho[2',3':4,5]imidazor[1,2-a] pyridine 850 mg (2.66 mmol) of 2-(3-chloro-2-pyridylamino)-3-chloro-1,4-dihydro-1,4-dioxonaphthalene in solution in 80 mL of glycerol is brought to 190° C. for 20 min. After complete cooling, the yellow precipitate obtained is filtered on fritted glass, washed w-th distilled water, and recrystallized in methanol after decoloration with animal black to produce 300 mg of 4-chloro-6,11-dihydro-6,11-dioxo-naptho[2',3':4,5]imidazo[1,2-a]pyridine in the form of yellow crystals.

Yield: 40%
Melting point: >300° C.
Rf: 0.10 (CH$_2$Cl$_2$)
MS (I.E.): m/z 282 (MH+.)
$^1$H-NMR (CD$_2$Cl$_2$): δ (ppm) 9.37 (dd, 1H, H-1, $J_{H1-H2}$=7.01 Hz, $J_{H1-H3}$=0.91 Hz) 8.26 (m, 2H, H-7, H-10) 7.81 (m, 2H, H-8, H-9) 7.71 (dd, 1H, H-3, $J_{H3-H2}$=7.63 Hz, $J_{H3-H1}$=0.91 Hz) 7.21 (t, 1H, H-2, $J_{H2-H3}$=7.32 Hz)
IR (KBr): ν (cm$^{-1}$) 1682, 1649 (C=O)

EXAMPLE 11

6,11-Dihydro-6,11-dioxo-2-fluoro-naphtho[2',3':4,5]imidazo[1,2-a] pyridine 0.98 g (8.75 mmol) of 2-amino-5-fluoropyridine is added to a suspension of 0.98 g (4.72 mmol) of 3-chloro-1,4-dihydro-1,4-dioxo-2-hydroxynaphthalene in solution in 10 mL of 1,2-dimethoxyethane. The reaction medium is brought to reflux for 23 h. After complete cooling, the medium is diluted in 10 mL of water. The precipitate is filtered, washed with water and heptane, and dried. The precipitate is diluted in dichloromethane, then the organic phase is washed successively with a saturated solution of sodium hydrogen carbonate, then sodium chloride. The organic phase is dried on sodium sulfate, filtered, then evaporated under reduced pressure. The raw product obtained is purified on a flash column (support: silica; eluent: dichloromethane/methanol, 99/1) to produce 0.03 g of 6,11-dihydro-6,11-dioxo-2-fluoro-naphtho[2',3':4,5]-imidazo[1,2a] pyridine in the form of yellow crystals after decoloration with animal black.

Yield: 2.3%
Rf: 0.55 (CH$_2$Cl$_2$/ethyl acetate, 96/4)
MS (I.E.): m/z 266 (M+.)
$^1$H-NMR (CD$_2$Cl$_2$): (ppm) 9.37 (m, 1H, H-1, $J_{H1-F}$=$J_{H1-H3}$=3.36 Hz) 8.25 (m, 2H, H-7, H-10) 7.91 (dd, 1H, H-4, $J_{H3-H4}$=9.76 Hz, $J_{H4-F}$=4.88 Hz) 7.80 (m, 2H, H-8, H-9) 7.56 (m, 1H, H-3, $J_{H3-H4}$=10.07 Hz, $J_{H3-F}$=7.94 Hz, $J_{H1-H3}$=2.75 Hz)
IR (KBr): ν (cm$^{-1}$) 1686, 1681 (C=O)

EXAMPLE 12

10-Chloro-5,6-dihydro-5,6-dioxo-naphtho[1',2':4,5]-imidazo[1,2-a] pyridine 3.27 g (25.9 mmol) of 2-amino-4-chloropyridine are added to a suspension of 6.64 g (28.9 mmol) of 2,3-dichloro-1,4-dihydro-1,4-dioxonaphthalene in 95 mL of glycerol. This mixture is heated to 205° C. for 10 min. The solution passes from yellow to dark brown.

After complete cooling, 5 mL of methanol are added to the reaction medium, then it is extracted with dichloromethane. The organic phase is dried, filtered, and evaporated to dryness.

This precipitate is purified on a cake (support: silica; eluent: heptane/dichloromethane/ethyl acetate, 100/0/0 to 0/95/5). The solid obtained is recrystallized in chlorobenzene to produce 0.16 g of 10-chloro-5,6-dihydro-5,6-dioxo-naphtho [1',2':4,5]imidazo-[1,2-a]pyridine in the form of orange crystals after treatment with animal black, then passage through a micropore filter.

Yield: 2%

Melting point: >300° C.

Rf: 0.30 ($CH_2Cl_2$/AcOEt, 96/4)

MS (I.E.): m/z 282/284 ($M^+$), 254/256 (M-CO)

$^1$H-NMR ($CD_2Cl_2$): δ (ppm) 9.28 (d, 1H, H-8, $J_{H8-H9}$=6.67 Hz) 8.28 (d, 1H, H-1, $J_{H1-H2}$=6.13 Hz) 8.20 (d, 1H, H-4, $J_{H3-H4}$=8.00 Hz) 7.93 (s, 1H, H-11) 7.82 (dd, 1H, H-2, $J_{H1-H2}$ or $J_{H2-H3}$=6.67 Hz) 7.65 (dd, 1H, H-3, $J_{H2-H3}$ or $J_{H3-H4}$=8.00 Hz) 7.30 (dd, 1H, H-9, $J_{H8-H9}$=6.93 Hz, $J_{H9-H11}$=2.13 Hz)

IR (KBr): ν ($cm^{-1}$) 1699, 1650 (C=O), 1626 (C=N)

EXAMPLE 13

4-Chloro-5,6-dihydro-5,6-dioxo-naptho(1',2':4,5]imidazo[1,2-a] pyridine

A catalytic quantity of palladium on 10% carbon is added to an orange suspension of 80 mg (0.27 mmol, 1 eq) of 5,6-dihydro-5,6-dioxo-4-nitro-naphtho[1',2':4,5]imidazo-[1,2-a]pyridine in ethanol under argon, and the mixture is brought to reflux. 26.4 μL of hydrazine monohydrate (0.27 mmol, 1 eq) are then added. The reaction mixture immediately becomes violet. After 30 min, 26.4 μL of hydrazine monohydrate (0.27 mmol, 1 eq) are added. After 1 h of reaction, the reaction mixture is allowed to return to ambient temperature and the brown-violet precipitate is filtered through dried cotton and solubilized in 5 mL of conc. hydrochloric acid. This solution is cooled to −10° C., then a solution consisting of 34 mg (0.49 mmol, 1.8 eq) of sodium nitrite and 5 mL of distilled water is added dropwise. The medium is left under agitation at this temperature for 0.5 h. The reaction medium is added dropwise to a solution cooled to −5° C., consisting of 18 mg (0.18 mmol, 0.7 eq) of copper chloride(I) and 5 mL of conc. hydrochloric acid. The agitation is continued for 2.5 h. The reaction mixture is then diluted in dichloromethane, washed successively with a saturated solution of sodium carbonate, then with distilled water. The organic phase is extracted, then dried on sodium sulfate and evaporated to dryness. The raw product is purified on preparation plates (support: silica, eluent: dichloromethane/methanol, 90/10) to produce 10 mg of 4-chloro-5,6-dihydro-5,6-dioxo-naphtho[1',2':4,5]imidazo[1,2-a]pyridine in the form of yellow crystals.

Yield: 14%

Melting point: >260° C.

Rf: 0.60 (Dichloromethane/Methanol, 98/2)

MS (APcI-) : m/z 282/284 (M−)

$^1$H-NMR ($CD_2Cl_2$): δ (ppm) 9.14 (d, 1H, H-8, $J_{H8-H9}$=6.43 Hz) 8.16 (d, 1H, H-1, $J_{H1-H2}$=7.54 Hz, $J_{H1-H3}$=1.51 Hz) 7.75 (d, 1H, H-11, $J_{H10-H1}$=8.41 Hz) 7.60 (t, 1H, H-10, $J_{H9-H10}$=$J_{H10-H11}$=8.40 Hz) 7.53 (t, 1H, H-2, $J_{H1-H2}$=$J_{H2-H3}$=7.91 Hz) 7.46 (d, 1H, H-3, $J_{H2-H3}$=7.51 Hz, $J_{H1-H3}$=1.51 Hz) 7.15 (t, 1H, H-9, $J_{H8-H9}$=$J_{H9-H10}$=6.43 Hz)

IR (KBr): ν ($cm^{-1}$) 1662 (C=O)

EXAMPLE 14

4-Bromo-5,6-dihydro-5,6-dioxo-naphtho[1',2':4,5]imidazo[1,2-a] pyridine

A catalytic quantity of palladium on 10% carbon is added to an orange suspension of 110 mg (0.37 mmol, 1 eq) of 5,6-dihydro-5,6-dioxo-4-nitro-naphtho[1',2':4,5]imidazo[1,2-a]pyridine in ethanol under argon and the mixture is brought to reflux. 36.3 μL of hydrazine monohydrate (0.37 mmol, 1 eq) are then added. The reaction mixture immediately becomes violet. After 30 min, 36.3 μL of hydrazine monohydrate (0.37 mmol, 1 eq) are added. After 1 h of reaction, the reaction mixture is allowed to return to ambient temperature and the brown-violet precipitate is filtered through dried cotton and solubilized in 15 mL of conc. hydrobromic acid. This solution is cooled to −15° C., then a solution consisting of 64 mg (0.93 mm mmol, 2.5 eq) of sodium nitrite and 5 mL of distilled water is added dropwise. The medium is left under agitation at this temperature for 1.5 h. The reaction medium is added dropwise to a solution cooled to −5° C., consisting of 21 mg (0.15 mmol, 0.4 eq) of copper(I) bromide and 5 mL of conc. hydrobromic acid. A violet solution is obtained and its agitation is continued for 2.5 h. The reaction medium is then diluted in dichloromethane, washed successively with a saturated solution of sodium carbonate, then with distilled water. The organic phase is extracted, dried on sodium sulfate and evaporated to dryness. The raw product is purified on preparation plates (support silica, eluent: dichloromethane/methanol, 95/5) to produce 30 mg of 4-bromo-5,6-dihydro-5,6-dioxo-naphtho[1',2':4,5]imidazo[1,2-a] pyridine in the form of yellow crystals.

Yield: 25%

Melting point: >260° C.

Rf: 0.60 (Dichloromethane/Methanol, 98/2)

MS (APcI+): m/z 326/328 ($M^+H^+$)

$^1$H-NMR($CD_2Cl_2$): δ (ppm) 9.13 (d, 1H, H-8, $J_{H8-H9}$=6.93 Hz) 8.21 (d, 1H, H-1, $J_{H1-H2}$=7.42 Hz) 7.75 (d, 1H, H-11, $J_{H10-H11}$=8.90 Hz) 7.71 (d, 1H, H-3, $J_{H2-H3}$=7.91 Hz) 7.60 (dd, 1H, H-10, $J_{H9-H10}$=$J_{H10-H11}$=8.90 Hz) 7.42 (t, 1H, H-2, $J_{H1-H2}$=$J_{H2-H3}$=7.42 Hz) 7.15 (t, 1H, H-9, $J_{H8-H9}$=$J_{H9-H10}$7.91 Hz)

IR (KBr): ν ($cm^{-1}$) 1610 (C=O)

EXAMPLE 15 OR EXAMPLE I 5,6-dihydro-5,6-dioxo-2-nitronaphtho[1',2':4,5]-imidazo[1,2-a] pyridine or 5,6-dihydro-5,6-dioxo-3-nitronaphtho[1',2':4,5]-imidazo[1,2-a] pyridine 0.42 g (4.41 mmol, 1.2 eq) of 2-aminopyridine is added to a solution of 1.00 g (3.67 mol, 1.0 eq) of 2,3-dichloro-1,4-dihydro-1,2-dioxo-6-nitronaphthalene in 200 mL of ethanol. The reaction mixture is brought to reflux for 24 h. The reaction is allowed to cool to ambient temperature; the orange precipitate formed during the reaction is filtered and purified on a flash column (support: silica 6–35 μm, h=30 cm, δ=9 cm; conditioning: heptane/ethyl acetate, 70/30; eluent: heptane/ethyl acetate, 70/30, then dichloromethane/ethyl acetate, 50/50) to produce 0.20 g of 5,6-dihydro-5,6-dioxo-2-nitronaphtho[1',2':4,5] imidazo[1,2-a]pyridine or 5,6-dihydro-5,6-dioxo-3-nitronaphtho[1',2':4,5]imidazo[1,2-a]pyridine in the form of ocher crystals after evaporation of the more polar fraction.

Yield: 18.5%

Melting point: >300° C.

Rf: 0.20 (heptane/ethyl acetate, 70/30)

MS (APcI-): m/z 293 (M−), 263 (M-NO)

$^1$H-NMR (DMSO-$d_6$): δ (ppm) 9.36 (d, 1H, H-8, $J_{H8-H9}$=7.62 Hz) 8.96 (s, 1H, H-1 of H-4, at α of the nitro) 8.57 (d, 1H, H-1 of H-4, $J_{H1-H2}=J_{H3-H4}=8.54$ Hz, at β of the nitro) 8.43 (d, 1H, H-2 of H-3, $J_{H1-H2}=J_{H3-H4}=8.54$ Hz) 7.92 (d, 1H; H-11, $J_{H10-H11}=7.63$ Hz) 7.75 (t, 1H, H-10, $J_{H9-H10}=J_{H10-H11}=7.63$ Hz) 7.32 (t, 1H, H-9, $J_{H8-H9}=J_{H9-H10}=7.63$ Hz)

IR (KBr): ν (cm$^{-1}$) 1649 (C=O), 1522 (NO$_2$)

EXAMPLE 16

6,11-dihydro-6,11-dioxo-7-nitronaphtho[2',3':4,5]imidazo [1,2-a] pyridine or
6,11-dihydro-6,11-dioxo-10-nitronaphtho[2',3':4,5]imidazo [1,2-a] pyridine 1.73 g (18 mmol, 1 eq) of 2-aminopyridine are added to a suspension of 5.00 g (18 mmol), 1 eq) of 2,3-dichloro-1,4-dihydro-1,4-dioxo-5-nitronaphthalene in 400 mL of ethanol. The mixture is brought to reflux for 5 h. After an orange precipitate appears, the reaction is allowed to cool to ambient temperature and the precipitate is filtered and purified on a flash column (support: silica 6–35 μm, h=45 cm, δ=16 cm; conditioning: heptane/ethyl acetate, 50/50; eluant: heptane/ethyl acetate, 50/50 to 70/30) to obtain 0.54 g of 6,11-dihydro-6,11-dioxo-7-nitronaphtho[2',3':4,5]imidazo[1,2-a] pyridine or 6,11-dihydro-6,11-dioxo-10-nitronaphtho[2',3':4,5]imidazo[1,2-a]pyridine, which after recrystallization in 1,2-dichlorobenzene produces 0.24 g of the expected product in the form of orange crystals.

Yield: 4.5%
Melting point: >300° C. (decomposition)
Rf: 0.40 (heptane/ethyl acetate, 70/30)
MS (APcI+): m/z 294 (M+H$^+$)
$^1$H-NMR (CDCl$_3$): δ (ppm) 9.35 (d, 1H, H-1, $J_{H1-H2}=6.38$ Hz) 8.33 (d, 1H, H-4, $J_{H3-H4}=6.39$ Hz) 7.89 (d, 1H, H-7 or H-10, $J_{H7-H8}$ of $J_{H9-H10}=8.44$ Hz) 7.73–7.65 (m, 3H, H-2, H-3, H-8 or H-9) 7.27 (m, 1H, H-8 or H-9, at β of the nitro)
IR (KBr): ν (cm$^{-1}$) 1660 (C=O), 1540 (NO$_2$)

EXAMPLE 17

6,11-dihydro-6,11-dioxo-8-fluoronaphtho[2',3':4,5]imidazo [1,2-a] pyridine or
6,11-dihydro-6,11-dioxo-9-fluoronaphtho[2',3':4,5]-imidazo [1,2-a]pyridine or
5,6-dihydro-5,6-dioxo-2-fluoronaphtho[1',2':4,5]-imidazo [1,2-a]pyridine or
5,6-dihydro-5,6-dioxo-3-fluoronaphtho[1',2':4,5]-imidazo [1,2-a]pyridine Intermediate product of synthesis:
2,3-dibromo-1,4-dihydro-1,4-dioxo-6-fluoronaphthalene 36 mL (710 mmol) of bromine are added to a solution of 1,4-dihydro-1,4-dioxo-6-fluoronaphthalene (No. CAS 148541-61-1) (12.5 g, 71 mmol) in chloroform (250 mL). The solution is brought to reflux for 12 h, then brought to ambient temperature. After bubbling in compressed air, the solution is concentrated under reduced pressure and the solid obtained is washed five times with heptane. 15.0 g of a beige powder of 2,3-dibromo-1,4-dihydro-1,4-dioxo-6-fluoronaphthalene are obtained.

Yield: 65%
Melting point: 158° C.
Rf: 0.80 (dichloromethane)
MS (APcI-): m/z 332, 334, 336 (M$^-$)
$^1$H-NMR (CDCl$_3$): δ (ppm) 8.22 (dd, 1H, H-8, $J_{H7-H8}=8.55$ Hz, $J_{H-F}=5.19$ Hz) 7.81 (dd, 1H, H-5, $J_{H-F}=8.55$ Hz, $J_{H5-H7}=2.75$ Hz) 7.45 (td, 1H, H-7, $J_{H-F}=J_{H7-H8}=8.55$ Hz, $J_{H5-H7}=2.75$ Hz)
IR (KBr): ν (cm$^{-1}$) 1680 (C=O)

6,11-dihydro-6,11-dioxo-8-fluoronaphtho[2',3':4,5]-imidazo [1,2-a]pyridine or
6,11-dihydro-6,11-dioxo-9-fluoronaphtho[2',3':4,5]-imidazo [1,2-a]pyridine or
5,6-dihydro-5,6-dioxo-2-fluoronaphtho[1',2':4,5]-imidazo [1,2-a]pyridine or
5,6-dihydro-5,6-dioxo-3-fluoronaphtho[1',2':4,5]-imidazo [1,2-a]pyridine 1.4 g (15 mmol, 2 eq) of 2-aminopyridine are added to a suspension of 2.5 g (7.5 mmol, 1.0 eq) of 2,3-dibromo-1,4-dihydro-1,4-dioxo-6-fluoronaphthalene in 50 mL of ethanol. The reaction mixture is brought to reflux of the solvent for 20 h, then brought to ambient temperature. The tan precipitate formed is filtered and washed profusely with ethanol. The solid obtained is purified by flash chromatography on a column of silica gel (support: silica 6–35 mm; (10 cm φ, 25 cm h; eluant: dichloromethane/ethyl acetate, 70/30). 494 mg of 6,11-dihydro-6,11-dioxo-8-fluoronaphtho[2',3':4,5] imidazo[1,2-a]pyridine or 6,11-dihydro-6,11-dioxo-9-fluoronaphtho[2',3':4,5]imidazo-[1,2-a] pyridine or 5,6-dihydro-5,6-dioxo-3-fluoronaphtho[1',2':4,5] imidazo[1,2-a]pyridine are obtained in the form of yellow crystals.

Yield: 42%
Melting point: >260° C.
Rf: 0.58 (dichloromethane/ethyl acetate, 70/30)
MS (APcI+): m/z 267 (M$^+$H$^+$)
$^1$H-NMR(CD$_2$Cl$_2$): δ (ppm) 9.20 (d, 1H, H-pyridyl, J=6.72 Hz) 8.07 (dd, 1H, H-aromatic, J=8.54 Hz, $J_{H-F}=5.49$ Hz) 7.81 (dd, 1H, H-aromatic, $J_{H-F}=8.54$ Hz, J=2.45 Hz) 7.78 (d, 1H, H-pyridyl, J=9.77 Hz) 7.63 (td, 1H, H-aromatic, $J_{H-F}=8.54$ Hz, J=2.45 Hz) 7.16 (m, 2H, H-pyridyl)
IR (KBr): ν (cm$^{-1}$) 1660 (C=O)

EXAMPLE 18

6,11-Dihydro-6,11-7-fluoronaphtho[2',3':4,5]imidazo [1,2-a] pyridine or
6,11-Dihydro-6,11-dioxo-10-fluoronaphtho[2',3':4,5]-imidazo[1,2-a]pyridine or
5,6-Dihydro-5,6-dioxo-1-fluoronaphtho[1',2':4,5]-imidazo [1,2-a]pyridine or
5,6-Dihydro-5,6-dioxo-4-fluoronaphtho[1',2':4,5]-imidazo [1,2-a]pyridine Intermediate synthesis product
2,3-Dibromo-1,4-dihydro-1,4-dioxo-5-fluoronaphthalene 7.34 mL (143 mmol) of bromine are added to a solution of 1,4-dihydro-1,4-dioxo-5-fluoronaphthalene (No. CAS 62784-46-7) at 2.45 g 71 mmol) in chloroform (60 mL). The solution is brought to reflux for 12 h, then brought to ambient temperature. After bubbling with compressed air, the solution is concentrated under reduced pressure and the beige solid product obtained is purified on a flash column (support: silica; conditioning: heptane; eluant: CH$_2$Cl$_2$/heptane) to produce 3.44 g of 2,3-dibromo-1,4-dihydro-1,4-dioxo-5-fluoronaphthalene in the form of beige crystals.

Yield: 74%
Melting point: 100° C.
Rf: 0.63 (dichloromethane/heptane: 80/20)
MS (I.E.): m/z 333, 335, 337 (MH$^{+\cdot}$)
NMR of $^1$H (CDCl$_3$): δ (ppm) 8.01 (d, 1H, H-8, $J_{H7-H8}=7.94$ Hz) 7.77 (m, 1H, H-7) 7.52 (m, 1H, H-6)
IR (KBr): ν (cm$^{-1}$) 1704 (C=O)

6,11-Dihydro-6,11-dioxo-7-fluoronaphtho[2',3':4,5]-imidazo[1,2-a]pyridine or
6,11-Dihydro-6,11-dioxo-10-fluoronaphtho[2',3':4,5]-imidazo[1,2-a]pyridine or
5,6-Dihydro-5,6-dioxo-1-fluoronaphtho[1',2':4,5]-imidazo [1,2-a]pyridine or
5,6-Dihydro-5,6-dioxo-4-fluoronaphtho[1',2':4,5]-imidazo [1,2-a]pyridine 0.885 g (9.4 mmol, 1 eq) of 2-aminopyridine is added to a suspension of 3.77 g (11.28 mmol, 1.2 eq) of 2,3-dibromo-1,4-dihydro-1,4-dioxo-5-fluoronaphthalene in 180 mL of ethanol.

The reaction mixture is brought to reflux, after 2 h it all passes into solution. A tan precipitate appears after the fifth hour. After 15 h of reflux, the ethanol is evaporated to dryness. A tan solid product is obtained and purified on a cake (support: silica 6–35 μm; conditioning: heptane; eluant: heptane/ethyl acetate: 90/10) to produce 375 mg of 6,11-dihydro-6,11-dioxo-7-fluoronaphtho[2',3':4,5]imidazo[1,2-a]pyridine, 6,11-dihydro-6,11-dioxo-10-fluoronaphtho[2',3':4,5]imidazo[1,2-a]pyridine or 5,6-dihydro-5,6-dioxo-4-fluoronaphtho[1',2':4,5]imidazo[1,2-a] pyridine in the form of yellow-orange crystals.

Yield: 15%
Melting point: >260° C.
Rf: 0.55 (AcOEt/Heptane, 70/30)
MS (I.E.): m/z 266 (M$^{+\cdot}$)
NMR of $^1$H (CD$_2$Cl$_2$): δ (ppm) 9.27 (d, 1H, H-pyridyl, J=6.74 Hz) 7.89 (dd, 1H, H-aromatic, J=7.02 Hz, J=1.22 Hz) 7.83 (d, 1H, H-pyridyl, J=9.13 Hz) 7.62 (m, 1H, H-pyridyl) 7.42 (m, 2H, H-aromatic) 7.19 (t, 1H, H-pyridyl, J=6.71 Hz)
IR (KBr): ν (cm$^{-1}$) 1700, 1645 (C=O)

EXAMPLE 19

4,9-Dichloro-5,6-dihydro-5,6-dioxonaphtho[1',2':4,5]imidazo [1,2-a]pyridine 125 mg (0.370 mmol, 1.0 eq) of 9-chloro-5,6-dihydro-5,6-dioxo-4-nitronaphtho[1'2':4,5]imidazo[1,2-a]pyridine are heated to reflux in 150 mL of absolute ethanol under argon, palladium on carbon is then added, after 30 min, one hydrazine equivalent is added, then a second equivalent, and after 15 min a third equivalent, i.e., a total of 56 μL (1.11 mmol, 3.0 eq). The medium is filtered cold.

The precipitate is solubilized in 20 mL of conc. hydrochloric acid. This solution is cooled to −17° C. and a solution consisting of 47 mg (0.67 mmol, 2.0 eq) of sodium nitrite and 5 mL of distilled water is added dropwise. The medium is agitated at this temperature for 0.5 h. The reaction medium is added dropwise to a solution cooled to −10C, comprised of 67 mg (0.67 mmol, 2 eq) of copper(I) chloride and 5 mL of conc. hydrochloric acid. The agitation is continued for 3 h. The reaction medium is filtered. The organic phase is neutralized by solid sodium carbonate, then extracted in dichloromethane. The organic phase is dried on sodium sulfate, filtered and evaporated to dryness. The raw product is purified on preparation plates (support: silica; eluant: dichloromethane/methanol, 98/2) to produce 8 mg of 4,9-dichloro-5,6-dihydro-5,6-dioxonaphtho[1',2':4,5]imidazo[1,2-a]pyridine in the form of orange crystals.

Yield: 4%
Melting point: >260° C.
Rf: 0.27 (Dichloromethane/Methanol, 98/2)
MS (I.E.): m/z 316, 318, 320 (M$^{+\cdot}$)
NMR of $^1$H (CD$_2$Cl$_2$): δ (ppm) 9.34 (d, 1H, H-8, J$_{H8-H10}$=1.74 Hz) 8.20 (d, 1H, H-1, J$_{H1-H2}$=7.0 Hz) 7.76 (m, 1H, H-11) 7.79 to 7,56 (m, 4H, H-10, H-2, H-3)
IR (KBr): ν (cm$^{-1}$) 1662 (C=O)

EXAMPLE 20

6,11-Dihydro-6,11-dioxo-7-methylnaphtho[2',3':4,5]imidazo[1,2-a]pyridine or
6,11-Dihydro-6,11-dioxo-10-methylnaphtho[2',3':4,5]imidazo[1,2-a]pyridine or
5,6-Dihydro-5,6-dioxo-1-methylnaphtho[1',2':4,5]-imidazo [1,2-a]pyridine or
5,6-Dihydro-5,6-dioxo-4-methylnaphtho[1',2':4,5]-imidazo [1,2-a]pyridine Intermediate synthesis product:
2,3-Dibromo-1,4-dihydro-1,4-dioxo-5-methylnaphthalene 200 mL of carbon tetrachloride, then 17.2 mL (337 mmol, 4 eq) of bromine are added to 14.5 g (84 mmol, 1 eq) of 1,4-dihydro-1,4-dioxo-5-methylnaphthalene. The solution becomes red, then 22.94 g (168 mmol, 2 eq) of sodium acetate are added. After 96 h of reflux, the reaction medium is filtered, washed with carbon tetrachloride and evaporated to dryness. The product is purified on a cake (φ=6.5 cm, height=5 cm, deposit=solid, support=silica, eluant CH$_2$Cl$_2$). A tan-orange paste is obtained after evaporation to dryness. A first crystallization with dichloromethane produces 8.25 g of 2,3-dibromo-1,4-dihydro-1,4-dioxo-5-methylnaphthalene in the form of yellow crystals; a second recrystallization with acetonitrile produces 11.90 g of 2,3-dibromo-1,4-dihydro-1,4-dioxo-5-methylnaphthalene in the form of yellow crystals.

Yield: 72%
Rf: 0.70 (ethyl acetate/heptane, 50/50)
MS (APcI-): m/z 328, 330, 332 (M$^-$)
$^1$H-NMR(CDCl$_3$): δ (ppm) 8.11 (dd, 1H, H-8, J$_{H7-H8}$=7.02 Hz, J$_{H6-H8}$=1.53 Hz) 7.63 (m, 2H, H-6, H-7) 2.76 (s, 3H, CH$_3$)
IR (KBr): ν (cm$^{-1}$) 1670 (C=O); 1570 (C=C)

6,11-dihydro-6,11-dioxo-7-methylnaphtho[2',3':4,5]-imidazo[1,2-a]pyridine or
6,11-dihydro-6,11-dioxo-10-methylnaphtho[2',3':4,5]-imidazo[1,2-a]pyridine or
5,6-dihydro-5,6-dioxo-1-methylnaphtho[1',2':4,5]-imidazo [1,2-a]pyridine or
5,6-dihydro-5,6-dioxo-4-methylnaphtho[1',2':4,5]-imidazo [1,2-a]pyridine 2.72 g (28.88 mmol, 2.4 eq) of 2-aminopyridine are added twice to a suspension of 4.00 g (12.12 mmol, 1 eq) of 2,3-dibromo-1,4-dihydro-1,4-dioxo-5-methylnaphthalene in 500 mL of ethanol. This mixture is brought to reflux for 48 h. After cooling to ambient temperature, the ethanol is eliminated by evaporation under reduced pressure. The 2,3-dibromo-1,4-dihydro-1,4-dioxo-5-methylnaphthalene that did not react is eliminated by precipitation in a CH$_2$Cl$_2$/heptane, 80/20 mixture. The raw product is purified by chromatography on a preparation plate (support: silica SIL G-200 UV254 2 mm; eluant: CH$_2$Cl$_2$/EtOH, 97/3) to produce 6,11-dihydro-6,11-dioxo-7-methylnaphtho[2',3':4,5] imidazo-[1,2-a]pyridine or 6,11-dihydro-6,11-dioxo-10-methylnaphtho[2',3':4,5]imidazo[1,2-a]pyridine or 5,6-dihydro-5,6-dioxo-4-methylnaphtho[1',2':4,5]-imidazo[1,2-a]pyridine in the form of yellowish-orange crystals.

Yield: 7%
Melting point: 218° C. (decomp)
Rf: 0.61 (CH$_2$Cl$_2$/EtOH, 97/3)
MS(I.E.): m/z 262 (M$^{+\cdot}$)
$^1$H-NMR (CD$_2$Cl$_2$): δ (ppm) 9.38 (d, 1H, H-pyridyl, J=6.64 Hz) 8.00 (d, 1H, H-pyridyl, J=6.64 Hz) 7.84 (d, 1H, H-aromatic, J=8.72 Hz) 7.67 (m, 1H, H-pyridyl) 7.52 (d, 1H, H-aromatic, J=7.47 Hz) 7.39 (t, 1H, H-aromatic, J=7.47 Hz) 7.23 (t, 1H, H-pyridyl, J=6.64 Hz) 2.98 (s, 3H, CH$_3$)
$^{13}$C-NMR(CDCl$_3$): δ (ppm) 139.34 (1C, C-aromatic) 132.30 (1C, C-pyridyl) 130.30 (1C, C-aromatic) 129.35 (1C, C-pyridyl) 129.25 (1C, C-aromatic) 118.91 (1C, C-pyridyl) 117.22 (1C, C-pyridyl) 23.18 (1C, CH$_3$)
IR (KBr): ν (cm$^{-1}$) 2940; 1745 (C=O); 1700 (C=C); 1650 (C=N)

EXAMPLE 21

2-chloro-6,11-dihydro-6,11-dioxo-7-methylnaphtho-[2',3':4,5]imidazo[1,2-a]pyridine or
2-chloro-6,11-dihydro-6,11-dioxo-10-methylnaphtho-[2',3':4,5]imidazo[1,2-a]pyridine or
9-chloro-5,6-dihydro-5,6-dioxo-1-methylnaphtho-[1',2':4,5]imidazo[1,2-a]pyridine or
9-chloro-5,6-dihydro-5,6-dioxo-4-methylnaphtho-[1',2':4,5]imidazo[1,2-a]pyridine 3.74 g (28.88 mmol, 2.4 eq) of 2-amino-5-chloropyridine are added twice to a suspension of 4.00 g (12.12 mmol, 1 eq) of 2,3-dibromo-1,4-dihydro-1,4-dioxo-5-methylnaphthalene in 500 mL of ethanol. This mixture is brought to reflux for 48 h. After cooling to ambient temperature, the ethanol is eliminated by evaporation under reduced pressure. The 2,3-dibromo-1,4-dihydro-1,4-dioxo-5-methylnaphthalene that had not reacted is eliminated by precipitation in a $CH_2Cl_2$/heptane, 80/20 mixture. The raw product is purified by chromatography on a column (support: silica 6–35 mm, conditioning: $CH_2Cl_2$/heptane, 90/10, eluant: $CH_2Cl_2$/AcOEt gradient, 100/0 to 50/50), then on a preparation plate (support: silica SIL G-200 UV 254 2 mm; eluant: $CH_2Cl_2$) to produce 2-chloro-6,11-dihydro-6,11-dioxo-7-methylnaphtho [2',3':4,5]imidazo[1,2-a]pyridin, 2-chloro-6,11-dihydro-6,11-dioxo-10-methylnaphtho[2',3':4,5]imidazo [1,20-a]pyridine, 9-chloro-5,6-dihydro-5,6-dioxo-1-methylnaphtho[1',2':4,5]imidazo [1,2-a]pyridine or 9-chloro-5,6-dihydro-5,6-dioxo-4-methylnaphtho [1',2':4,5]imidazo[1,2-a]pyridine in the form of orange crystals.

Yield: 6%
Rf: 0.76 ($CH_2Cl_2$/EtOH, 97/3)
MS(I.E.): m/z 296 et 298 (M+·)
$^1$H-NMR($CD_2Cl_2$): δ (ppm) 9.33 (d, 1H, H-pyridyl, J=1.83 Hz) 7.91 (m, 1H, H-aromatic) 7.69 (dd, 1H, H-pyridyl, J=0.91 Hz, J=9.46 Hz) 7.53 (dd, 1H, H-pyridyl, J=2.14 Hz, J=9.46 Hz) 7.42 (m, 1H, H-aromatic) 7.31 (t, 1H, H-aromatic, J=7.63 Hz) 2.86 (s, 3H, $CH_3$)

EXAMPLE 22

6,11-dihydro-6,11-dioxo-8-methylnaphtho[2',3':4,5]-imidazo[1,2-a]pyridine or
6,11-dihydro-6,11-dioxo-9-methylnaphtho[2',3':4,5]-imidazo[1,2-a]pyridine or
5,6-dihydro-5,6-dioxo-2-methylnaphtho[1',2':4,5]-imidazo[1,2-a]pyridine or
5,6-dihydro-5,6-dioxo-3-methylnaphtho[1',2':4,5]-imidazo[1,2-a]pyridine 2.72 g (28.88 mol, 2.4 eq) of 2-aminopyridine are added twice to a suspension of 4.00 g (12.12 mmol, 1 eq) of 2,3-dibromo-1,4-dihydro-1,4-dioxo-6-methylnaphthalene (No. CAS 72364-92-2) in 500 mL of ethanol. This mixture is brought to reflux for 48 h. After cooling to ambient temperature, the ethanol is eliminated by evaporation, under reduced pressure. The 2,3-dibromo-1,4-dihydro-1,4-dioxo-6-methylnaphthalene that had not reacted is eliminated by precipitation in a $CH_2Cl_2$/heptane, 70/30 mixture. The raw product is purified by two successive chromatographies on a preparation plate (support: silica SIL G-200 UV254 2 mm; eluant first plate: $CH_2Cl_2$/MeOH, 97/3, and eluant second plate: heptane/AcOEt, 50/60) to produce 6,11-dihydro-6,11-dioxo-8-methylnaphtho[2,,3':4,5]imidazo[1,2-a]pyridine, 6,11-dihydro-6,11-dioxo-9-methylnaphtho[2',3':4,5] imidazo[1,2-a] pyridine, 5,6-dihydro-5,6-dioxo-2-methylnaphtho[1',2':4,5] imidazo[1,2-a]pyridine or 5,6-dihydro-5,6-dioxo-3-methylnaphth [1',2':4,5]imidazo[1,2-a]pyridine in the form of orange crystals.

Yield: 18%
Melting point: 244° C. (decomp.)
Rf: 0.67 ($CH_2Cl_2$/MeOH, 95/5)
MS(I.E.): m/z 262 (M+·)
$^1$H-NMR($CD_2Cl_2$): δ (ppm) 9.36 (d, 1H, H-pyridyl, J=6.64 Hz) 8.12 (sl, 1H, H-α of $CH_3$) 8.08 (d, 1H, H-β of $CH_3$, J=7.88 Hz) 7.91 (d, 1H, H-pyridyl, J=9.14 Hz) 7.75 (ddd, 1H, H-pyridyl, J=9.14 Hz, J=7.05 Hz, J=1.24 Hz) 7.44 (dd, 1H, H-α of $CH_3$, J=7.89 Hz, J=1.24 Hz) 7.32 (td, 1H, H-pyridyl, J=7.05 Hz, J=7.89 Hz) 2.60 (s, 3H, $CH_3$) $^{13}$C-NMR($CDCl_3$): δ (ppm) 132.34 (1C, C-aromatic) 131.66 (1C, C-aromatic) 130.27 (1C, C-pyridyl) 129.21 (1C, C-pyridyl) 125.53 (1C, C-aromatic) 118.45 (1C, C-pyridyl) 116.93 (1C, C-pyridyl) 22.06 (1C, $CH_3$)
IR (KBr): ν ($cm^{-1}$) 1700 (C=C); 1650 (C=N); 1600

EXAMPLE a 5,6-Dihydro-5,6-dioxo-naphtho[1',2':4,5]imidazo[1,2-a]pyridine
Reference: C.A. 58 12542e
Yield: 44%
Melting point: >260° C.
Rf: 0.50 ($CH_2Cl_2$/Methanol, 95/5)
MS (I.E.): m/z 248 (M+.)
$^1$H-NMR ($CDCl_3$): (ppm) 9.07 (d, 1H, H-8, $J_{H8-H9}$=6.73 Hz) 8.06 (d, 1H, H-1, $J_{H1-H2}$=7.53 Hz) 7.94 (d, 1H, H-4, $J_{H3-H4}$=7.99 Hz) 7.63 (d, 1H, H-11, $J_{H10-H11}$=8.73 Hz) 7.51 (dt, 1H, H-2, $J_{H1-H2}$=$J_{H2-H3}$=7.43 Hz, $J_{H2-H4}$=1.02 Hz) 7.41 (dt, 1H, H-10, $J_{H9-H10}$=$J_{H10-H11}$=7.30 Hz, $J_{H8-H10}$=1.22 Hz) 7.33 (dt, 1H, H-3, $J_{H2-H3}$=$J_{H3-H4}$=7.95 Hz, $J_{H1-H3}$=1.03 Hz) 6.96 (dd, 1H, H-9, $J_{H8-H9}$=6.81 Hz
$^{13}$C-NMR($CDCl_3$): (ppm) 181.5 (1C, C-5) 153.7 (1C, C-12a) 150.1 (1C, C-11a) 135.65 (1C, C-2) 132.50 (1C, C-10) 131.09 (1C, C-3) 130.44 (1C, C-4) 129.34 (1C, C-8) 124.94 (1C, C-1) 118.49 (1C, C-11) 5 116.50 (1C, C-9)
IR (KBr): ν ($cm^{-1}$) 1685, 1650 (C=O)

EXAMPLE b 5,6-Dihydro-5,6-dioxo-8-methylnaphtho[1',2':4,5]-imidazo[1,2-a]pyridine
Reference: C.A. 55 P25998e
Yield: 52%
Melting point: >260° C.
Rf: 0.55 ($CH_2Cl_2$/Methanol, 97/3)
MS (I.E.): m/z 262 (M+.)
$^1$H-NMR($CDCl_3$): (ppm) 8.21 (m, 2H, H-1, H-4) 7.72 (m, 3H, H-2, H-3, H-11) 7.51 (m, 1H, H-10) 6.97 (d, 1H, H-9, $J_{H9-H10}$=7.02 Hz) 3.12 (s, 3H, $CH_3$) $^{13}$C-NMR($CDCl_3$): (ppm) 183.01 (1C, Cquat) 173.45 (1C, Cquat) 151.45, 149.64 (2C, Cquat) 141.32 (1C, Cquat) 134.33, 133.06 (2C, C-2, C-3) 131.40, 126.71 (3C, C-1, C-4, Cquat) 127.36 (1C, C-10) 124.15 (1C, Cquat) 119.92 (1C, Cquat) 118.09 (1C, C-11) 117.24 (1C, C-9) 23.55 (1C, $CH_3$)
IR (KBr): ν ($cm^{-1}$) 1701, 1656 (C=O)

EXAMPLE c

9-Chloro-5,6-dihydro-5,6-dioxo-naphtho[1',2':4,5]-imidazo[1,2-a]pyridine
Reference: C.A. 55 P25998e
Yield: 61%
Melting point: >260° C.
Rf: 0.40 ($CH_2Cl_2$/Methanol, 98/2)
MS (I.E.): m/z 282 (M+.)
$^1$H-NMR ($CDCl_3$): (ppm)
9.31 (dd, 1H, H-8, $J_{H8-H10}$=2.06 Hz, $J_{H8-H11}$=0.72 Hz) 8.14 (dd, 1H, H-1, $J_{H1-H2}$=7.70 Hz, $J_{H1-H3}$=0.83 Hz) 8.11 (dd, 1H, H-4, $J_{H3-H4}$=7.79 Hz, $J_{H2-H4}$=1.04 Hz) 7.73 (dd, 1H, H-11, $J_{H10-H11}$=9.46 Hz, $J_{H8-H11}$=0.69 Hz) 7.68 (dt, 1H, H-2, $J_{H1-H2}$=$J_{H2-H3}$=7.57 Hz, $J_{H2-H4}$=1.31 Hz) 7.58 (dd, 1H, H-10, $J_{H10-H11}$=9.45 Hz, $J_{H8-H10}$=2.05 Hz) 7.51 (dt, 1H, H-3, $J_{H2-H3}$=$J_{H3-H4}$=7.66 Hz, $J_{H1-H3}$=1.20 Hz)
$^{13}$C-NMR($CDCl_3$): (ppm) 181.45 (1C, C-5) 167.70 (1C, C-6a) 154.27 (1C, C-12a) 148.61 (1C, C-11a) 135.46 (1C, C-2) 133.13 (1C, C-10) 131.17 (1C, C-12b) 130.97 (1C, C-3) 130.79 (1C, C-4a) 130.31 (1C, C-4) 126.89 (1C, C-8) 124.95 (1C, C-9) 124.75 (1C, C-1) 118.34 (1C, C-11)
IR (KBr): ν ($cm^{-1}$) 1680, 1650 (C=O)

EXAMPLE d
9-Bromo-5,6-dihydro-5,6-dioxo-naphtho[1',2':4,5]-imidazo[1,2-a]pyridine
Reference: C.A. 55 P25998e
Yield: 21%
Melting point: 280° C.
Rf: 0.48 (CH$_2$Cl$_2$/Ethyl Acetate, 90/10)
MS (I.E.): m/z 326, 328 (M+.)
$^1$H-NMR(270 Mhz, CDCl$_3$): δ (ppm) 9.45 (s, 1H, H-8) 8.17 (t, 2H, H-1, H-4, J$_{H1-H2}$=J$_{H3-H4}$=7.63 Hz) 7.71 (m, 3H, H-2, H-10, H-11) 7.54 (t, 1H, H-3, J$_{H2-H3}$=J$_{H8-H4}$=6.94 Hz)
$^{13}$C-NMR(270 MHz, CDCl$_3$): δ (ppm) 135.5, 135.4 (2C, C-2, C-10) 131.0 (1C, C-3) 130.4 (1C, C-4) 129.0 (1C, C-8) 124.8 (1C, C-1) 118.6 (1C, C-11) 111.4 (1C, C-9)
IR (KBr): µ (cm$^{-1}$) 1650, 1622 (C=O)

EXAMPLE e
5,6-Dihydro-5,6-dioxo-4-nitro-naphtho[1',2':4,5]-imidazo[1,2-a]pyridine
Reference: C.A. 55 P25998h
Yield: 25%
Melting point: >260° C.
Rf: 0.34 (CH$_2$Cl$_2$/Methanol, 98/2)
MS (I.E.): m/z 293 (M+.)
$^1$H-NMR (CDCl$_3$): δ (ppm) 9.28 (d, 1H, H-8, J$_{H9—H9}$=6.41 Hz) 8.41 (d, 1H, H-1, J$_{H1-H2}$=7.93 Hz) 7.85 (m, 2H, H-11) 7.72 (t, 1H, H-10, J$_{H9-H10}$=J$_{H10-H11}$=7.63 Hz) 7.50 (d, 1H, H-3, J$_{H3-H4}$=7.94 Hz) 7.27 (t, 1H, H-9, J$_{H8-H9}$=J$_{H9-H10}$=6.10 Hz)
13C-NMR(CDCl$_3$): δ (ppm) 187.68, 182.16 (2C, C-5, C-6) 177.00 (1C, Cquat) 144.90 (1C, C-4) 136.06 (1C, C-2) 132.86,(1C, C-10) 129.17 (1C, C-8) 126.99 (1C, C-1) 124.54 (1C, C-3) 118.58 (1C, C-11) 117.40 (1C, C-9)
IR (KBr): µ (cm$^{-1}$) 1694, 1651 (C=O)

EXAMPLE f
5,6-Dihydro-5,6-dioxo-naphtho[1',2':4,5]-imidazo[1,2-a]pyridine
Reference: C.A. 55 P25998f
Yield: 37%
Melting point: >260° C.
Rf: 0.60 (CH$_2$Cl$_2$/Methanol, 98/2)
MS (I.E.): m/z 249 (M+.)
$^1$H-NMR(CDCl$_3$): δ (ppm) 9.52 (d, 1H, H-8, J$_{H9—H9}$=5.00 Hz) 8.88 (d, 1H, H-10, J$_{H9-H10}$=5.00 Hz) 8.20, 8.06 (2d, 2H, H-1, H-4, J$_{H1-H2}$=J$_{H3-H4}$=7.63 Hz) 7.78, 7.60 (2d, 2H, H-2, H-3) 7.45 (m, 1H, H-9)
13C-NMR(CDCl$_3$): δ (ppm) 169.33 (1C, Cquat) 155.58 (1C, Cquat) 136.24 (1C, C10) 135.74, 131.46 (2C, C-1, C-3) 130.41, 125.70 (2C, C-1, C-4) 125.53 (1C, Cquat) 112.41 (1C, C-9)
IR (KBr): µ (cm$^{-1}$) 1698, 1653 (C=O)

EXAMPLE g
6,11-Dihydro-6,11-dioxo-naphtho[2',3':4,5]-imidazo[1,2-a]pyridine
Reference: C.A. 55 21115b
Yield: 6%
Melting point: 293° C.
Rf: 0.10 (CH$_2$Cl$_2$/Ethyl Acetate, 96/4)
MS (I.E.): m/z 248 (M+.)
$^1$H-NMR(CDCl$_3$): δ (ppm) 9.41 (d, 1H, H-1, J$_{H1-H2}$=6.72 Hz) 8.25 (m, 2H, H-7, H-10) 7.92 (d, 1H, H-4, J$_{H3-H4}$=9.15 Hz) 7.79 (m, 2H, H-8, H-9) 7.66(m, 1H, H-2, J$_{H1-H2}$=J$_{H2-H3}$=7.02 Hz, J$_{H2-H4}$=1.22 Hz) 7.28 (dt, 1H, H-3, J$_{H2-H3}$=J$_{H3-H4}$=7.02 Hz, J$_{H1-H3}$=0.91 Hz)
13C-NMR(CDCl$_3$): δ (ppm) 182.94 (1C, C=0) 176.30 (1C, C=0) 149.39, 146.19 (2C, C-5a, C-11a) 134.47 (1C,C-8 ou C-9) 134.27, 134.11 (2C, C-6a, C-10a) 134.00 (1C, C-8 ou C-9) 131.23 (1C, C-3) 120.83 (1C, C-1) 127.55, 126.82 (2C, C-7, C-10) 119.90 (1C, C-2) 117.46 (1C, C-4)
IR (KBr): µ (cm$^{-1}$) 1686, 1644 (C=O)

EXAMPLE h
6,11-Dihydro-6,11-dioxo-pyrido[1',2':1,2]-imidazo[5,4-g]quinoline
Reference: C.A. 116 151679t
Yield: 31%
Melting point: 260° C.
Rf: 0.51 (CH$_2$Cl$_2$/Ethanol, 94/6)
MS (I.E.): m/z 249 (M+.)
$^1$H-NMR(CDCl$_3$): δ (ppm) 9.39 (d, 1H, H-1, J$_{H1-H2}$=7.02 Hz) 9.04 (d, 1H, H-8, J$_{H8-H9}$=5.19 Hz) 8.60 (d, 1H, H-10, J$_{H9-H10}$=7.63 Hz) 7.99 (d, 1H, H-4, J$_{H3-H4}$=9.16 Hz) 7.71 (m, 2H, H-2, H-9) 7.33 (m, 1H, H-3)
13C-NMR(CDCl$_3$): δ (ppm) 154.19 (1C, C-8) 134.72 (1C, C-10) 131.73 (1C, C-3) 128.82 (1C, C-1) 127.86 (1C, C-9) 120.04 (1C, C-4) 117.82 (1C, C-2)
IR (KBr): µ (cm$^{-1}$) 1697, 1644 (C=O)

Pharmacological properties

The study of the compounds in the present invention and of their derived salts has demonstrated that they have various pharmacological properties. Thus, they are selectively vasotonic, not affecting the arterial system except in concentrations much greater than those active on the veins with the exception of certain arteries, the cerebral arteries in particular. The compounds show no, or at the most, very weak affinity for the great majority of known receptors. Furthermore, they increase capillary resistance and diminish vascular hyperpermeability induced by certain inflammatory agents.

These properties become evident in such mammals as hamsters, rats, guinea pigs, and rabbits, whether in vitro (isolated vessels or vascular networks) or in vivo.

For the in vitro studies, the compounds are made soluble in a pure aqueous solution or a solution containing DMSO (dimethyl sulfoxide).

As for the in vivo studies, they are administered intravenously or intraperitoneally in the form of an aqueous solution with or without DMSO, or orally in a 1% carboxymethylcellulose suspension, administered with the use of a force-feed probe at a volume of 10 mL/kg.

Pharmacological study models
Contractile effects

Contractile effects are measured, in vitro and under static conditions, on capacitance or resistance vascular rings of the saphenous, femoral, jugular, mesenteric, and caval veins; and on the femoral, carotid, basilar, mesenteric, and thoracic or abdominal aortic arteries, in rats (Wistar, 200 to 250 g), rabbits (New Zealand, 2 to 2.5 kg), and guinea pigs (Dunkin Hartley, 250 to 300 g).

The rings are placed in an isolated organ chamber (25 mL for capacitance vessels and 2.5 mL for resistance vessels, as per Mulvany), kept in isometric conditions by two stiff cables inserted into the interior of the vessel, avoiding any damage to the endothelium. The vessels are washed in a modified Krebbs solution (in mM: NaCl=118; KCl=4.6; ClCl$_2$=2.5; MgSO$_4$=1.2; KH$_2$PO$_4$=1.17; NcHCO$_3$=25; glucose=11), permanently aerated by a gaseous mixture at 95% O$_2$ and 5% CO$_2$, at pH=7.4 and set thermostatically at 37° C. The rings are taken to their optimal point of the tension-length ratio.

The tensions developed generate an electrical signal through a strength sensor (Wheatstone bridge). This signal is amplified before either being displayed on a Kipp & Zonen recorder or is digitalized for computer analysis (IOS, EMKA). The pharmacological studies are carried out after some preliminary contractile stimulations standardized by a depolarizing solution (hyperpotassic solution obtained by replacing NaCl by KCl in equimolar quantities), rinses, and balancing periods in pure physiological solution. Presence of the endothelium is verified by the relaxation induced by increasing concentrations of acetylcholine after stabilization of a vascular precontraction.

The contraction forces developed by the vascular rings in response to the different compounds are studied on quiescent or electrically stimulated (5–8 Hz) vessels, using a hyperpotassic depolarizing physiological solution (KCl: 20, 40 mM), using noradrenaline (increasing concentrations), or using serotonin (increasing concentrations).

The contractions are expressed in mg of force or as a percentage of maximum contraction at depolarization by a hyperpotassic physiological solution.

The contractile effects are also measured in vitro in flux dynamic conditions, via the pressure developed by the vascular networks perfused at a constant rate. At the mesenteric level, venoselectivity is studied by the simultaneous and separate double perfusion model, developed by T. Warner (British Journal of Pharmacology, 1990, 99, 427–433). Separation of the two networks is obtained by cutting the vessels and tissues along the length of the intestinal border. The networks are perfused at $2$ mL·min$^{-1}$ by an aerated Krebbs solution (37.5° C.) at 95% $O_2$ and 5% $CO_2$.

In vivo, the arterial and venous pressures are measured in an anesthetized animal, under basal conditions and after circulatory arrest provoked by inflating a balloon catheter inserted at the level of the right atrium. At the moment of cardiac arrest, the venous pressure (average circulation refill pressure at a constant blood volume) is calculated from the venous and arterial pressures at equilibrium and corrected as a function of the relative differences of compliance between the networks (Samar Coleman, American Journal of Physiology, 234: H94–100, 1978; Yamamoto et al., American Journal of Physiology, 238: H823–828, 1980).

In the case of the conscious animal, blood pressure is taken by the classical method based on Riva Rocci, by analysis of the acoustical wave transmitted at the arterial level and transformed by a ceramic piezo transducer placed on the rat's tail, below a sleeve automatically inflated by a pressure generator.

At the microcirculatory level, section variations in the venules and arterioles are studied in vivo by the method of placing a cutaneous chamber on the back of a conscious hamster, after videomicroscopy (Letz Ergolux microscope equipped with a halogen source for lighting and an HPR 610 black-and-white CDD video camera) and computer analysis (Visicap, Pack JCAP software) of the images.

After anesthesia by sodium pentobarbital (60 mg/kg, i.p.), the animal's back is shaved and depilated so that an observation chamber (Prof. Gebhard, Heidelberg) could be placed on the skin of the back. Both parts of the chamber are sown together after careful removal of a certain level of skin thickness that could impede observation. A jugular catheter is placed for i.v. administration of the products 48 h after the operation.

Effects on induced capillary hyperpermeability

Vascular permeability is studied in vivo by measuring albumin extravasation, the quantity of which is determined by a coloring agent bonded to the albumin (Evans Blue). Hyperpermeability is induced by the intradermal injection of a histamine, bradykinin, or zymosan solution.

The technique is derived from that described by Beach and Steinetz, Journal of Pharmacology and Experimental Therapy, 131: 400–406, 1961.

The rats (Wistars, 200 to 230 g) are shaved on the abdominal wall 1 h before the start of the experiment. The product to be tested is injected i.p. or orally 1–4 h prior to sacrificing. The rats are anesthetized using a halothane mixture. They then receive an intradermal injection in the abdomen of 0.10 to 0.15 mL of an inflammatory agent (by histamine 6.7 or 10 $\mu$g) and an i.v. injection of 1 mL of Evans blue 0.5% solution in the vein of the penis. These injections are carried out 30 min prior to sacrificing.

30 min after these two injections, the rats are sacrificed by cervical dislocation.

At the locus of injection of the inflammatory agent, the skin is cut off and placed in ground-neck glass tubes containing 3 mL of fuming hydrochloric acid. Digestion of the skin is carried out by contact [with HCl] of at least 1 h in a double boiler at 37° C.; 3 mL of benzalkonium chloride at 12.8% are then added. After leaving undisturbed for 30 min, 7 mL of dichloromethane are added. The tubes are periodically agitated for 1 h. The aqueous phase is eliminated by aspiration and the organic dichloromethane phase is filtered. The optical densities are quantified by absorption spectrophotometry at a 620 nm wavelength, against a blank [control] containing only dichloromethane.

The averages for optical density of the different lots of experimental and control animals are calculated, then the variation between the data for the experimental animals and those for the control animals is calculated.

The effect of the compounds on the induced hyperpermeability by inflammatory agents, such as histamine and bradykinin, is likewise studied after i.v. injection by bolus in the hamster dorsal cutaneous chamber model and according to the method developed by Gimeno et al., previously described (A new technique using intravital videomicroscoy for macromolecular permeability measurement, 18th European Microcirculation Congress, Rome, 1994) by videomicroscopy and image analysis by quantification of intra- and extravascular fluorescence distribution of the fluorescent marker (FITC-Dextran), injected by bolus by a jugular catheter (63 mg/kg for a volume defined at 1 mL/kg). The microscope is equipped with a fluorescene source and a combination cf filters (450–490-nm blue excitation and 515-nm stop filter).

Effects on capillary resistance:

The increase in capillary resistance is detected by the change in the petechial index (negative pressure inducing the extravasation of erythrocytes), measured by a method derived from Parrot's angiosterrometer.

The study is carried out on male Wistar rats weighing an average of 200 g (aged approximately 6 weeks). The lower back area is shaved, then depilated with the use of a paste based on a by-product of thioglycolic acid and calcium hydroxide. After approximately 30 min, the skin is rinsed abundantly and dried.

On the day of the study, the rats are kept nonconstrained. A low pressure of 80 mm of mercury is applied. If the petechiae (erythrocyte extravasation) do not appear withing 15 sec, the low pressure is increased by compensation, keeping the suction cup in the same place.

The minimum low pressure at which the petechiae appear expressed in mm of mercury, the value of the base capillary resistance (before any treatment). Two measurements are carried out for each trial on different places on the back. The rats are treated orally. After a predetermined amount of time (generally 2, 4, or 6 h) after the treatment, the test is renewed on different areas of skin, until petechiae appear, yielding a new low pressure index. All measurements are carried out in the blind mode.

The variation between the means of the base capillary resistance and post-treatment capillary resistance is calculated for the experimental animals, for each treatment time and compared to the control group (excipient only) or the reference group.

Effects on induced pleurisy in rats:

The antiinflamatory activity of the compounds is also studied by measuring edema and leucocyte migration inhibition after the induction of pleurisy in rats by the injection of carrageenin into the pleural cavity (Almeida et al., Journal of Pharmacology and Experimental Therapy, 214: 74, 1980).

The rats are treated orally with the compounds 2 h before the injection of carrageenin, as well as 2 and 4 h after such injection. After a predetermined amount of time (6 h) following the induction of pleurisy, the rats are sacrificed, the pleural liquid is recovered by aspiration, and its volume is measured. The leucocytes are counted by a cell counter.

The results are expressed as the number of leucocytes in the exudate for each 100 g of weight of the animal, and compared to the control group.

Examples of pharmacological effects:

The compounds of the invention and their derived salts selectively increase, in the majority of cases, the contraction of animal veins produced by noradrenaline, by electrical stimulation, or by a depolarizing hyperpotassic solution. By way of example, there is the contractile effect of different compounds on the saphenous vein of rabbits, precontracted by a depolarizing physiological solution with a potassium concentration equal to 40 mM; the maximum effect produced by each compound is expressed as the percentage of maximum contraction induced by the depolarizing hyperpotassic solutions and in $ED_{50}$ values:

| Compound   | Emax(% of maximum contr.) | $ED_{50}$ (nM) |
|------------|---------------------------|----------------|
| Example a  | 32 ± 7                    | 306            |
| Example c  | 27 ± 4                    | 157            |
| Example f  | 56 ± 7                    | 450            |
| Example h  | 18 ± 3                    | 67             |
| Example 1  | 20 ± 4                    | 170            |
| Example 2  | 28 ± 4                    | 271            |
| Example 3  | 18 ± 4                    | 200            |
| Example 12 | 13 ± 3                    | 58             |

By way of example, the oral administration of certain compounds of the invention and their derived salts increases the capillary resistance in rats at doses generally between 0.01 and 5 mg/kg:

| Compound  |           | Effect at 4 hours (in % of control) | Effect at 6 hours (in % of control) |
|-----------|-----------|-------------------------------------|-------------------------------------|
| Example 2 | 5 mg/kg   | 11                                  | 13                                  |
| Example c | 5 mg/kg   | 17                                  | 10                                  |
| Example c | 0.1 mg/kg | 19                                  | 29                                  |
| Example c | 0.1 mg/kg | 0                                   | 17                                  |
| Example h | 0.1 mg/kg | 19                                  | 13                                  |

By way of illustration, the oral administration of certain compounds of the invention and their derived salts reduce inflammatory hyperpermeability induced by zymosan in rats in doses generally between 0.01 and 5 mg/kg:

| Compound  |           | Effect at 2 hours (in % of control) | Effect at 4 hours (in % of control) |
|-----------|-----------|-------------------------------------|-------------------------------------|
| Example a | 5 mg/kg   | −1                                  | −28                                 |
| Example c | 0.1 mg/kg | −14                                 | −11                                 |
| Example h | 0.1 mg/kg | −23                                 | −5                                  |
| Example 2 | 0.1 mg/kg | −10                                 | −15                                 |
| Example 3 | 5 mg/kg   | −13                                 | −12                                 |

Furthermore, the compounds of the invention and their derived salts have a very low toxicity. For example, after a single oral administration of 1 g/kg in mice, no toxic effect was observable and no mortality was observable for the majority of compounds, especially for Example a, Example c, and Example 2.

Among the preferred compounds of the invention, Example c is especially singled out.

The foregoing demonstrates that the compounds of the invention and their derived salts may be used in human and animal therapy. They are specifically indicated in functional organic venous insufficiency and in hemorrhoidal pathologies due to their vascular and anti-inflamatory components, as well as in typically inflammatory disorders and in states of shock caused by a significant drop in blood pressure. In the latter case, an improvement in venous return may maintain the heart rate and, as a consequence, maintain the blood pressure.

Functional venous insufficiency is characterized by dilation and hyperdistensibility of the superficial veins in the legs, edema, and impatience [unconfirmed translation] paresthesia of the restless leg type. This type of pathology may evolve toward organic venous insufficiency characterized by the development of varicose veins, valvular incontinence, or towards thrombophlebitis and trophic disorders leading to ulcerative lesions.

In this venous pathology, an inflammatory component is established in the first stages and becomes more clearly detectable in the advanced stages.

Due to their effects on vasoconstrictors, anti-inflammatories, especially on vascular hyperpermeability, and their contractile effects on cerebral arteries, the compounds of the invention and their derived salts are also indicated for migraine.

The present invention then includes the use of the above-mentioned compounds and their derived salts as active substances for the preparation of medications and pharmaceutical compositions for human and veterinary use, having at least one of said compounds and salts associated with a physiologically acceptable support or diluent.

The form of these medications and pharmaceutical compositions will obviously depend on the desired manner of administration—oral, parenteral, topical (cutaneous), and rectal—and they may be formulated according to classical techniques, making use of the usual supports and vehicles.

Thus, in the case of oral administration, they may take the form of pills, tablets, gels, solutions, syrups, emulsions, suspensions, powders, granules, soft capsules, lyophilizates, microcapsules, or micro granules.

Pills, tablets, and gels contain the active ingredient together with a diluent (for example, lactose, dextrose, sucrose, mannitol, maltitol, xylitol, sorbitol, or cellulose), a lubricant (for example silica, talc, or stearate), a bonding agent (for example, starch, methylcellulose or gum arabic), and/or a disintegration agent (alginate, for example); they are manufactured by known methods, for example, mixing, granulation, lozenge-formation, coating, compression, etc.

Syrups may contain, as a support, glycerol, mannitol, and/or sorbitol. Solutions and suspensions may contain water and other physiologically compatible solvents and a support such as a natural gum, agar—agar, sodium alginate, or polyvinyl alcohol.

For parenteral administration, the medications and compositions may take the form of solutions, emulsions, or suspensions containing the active ingredient and an appropriate support or solvent such as sterile water or sterile isotonic solutions.

For cutaneous application, the medications and compositions may take the form of an ointment, creme, or gel, in the form of an emulsion or suspension, solution, mousse, or powder.

For rectal application, the medications and compositions may take the form of a capsule, creme, emulsion, gel, mousse, paste, or suppository.

We claim:

1. A method of treatment for an illness linked to alteration in venous function or inflammatory edema which comprises administering an effective amount of a tetracylic derivative or, a pharmaceutically acceptable salt thereof, having the general formula:

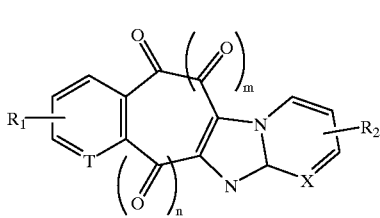

(I)

in which, independently of the other:
X is a carbon atom,
T is a carbon atom,
$R_1$ is an atom of hydrogen, an atom of halogen, or a $C_1$ to $C_5$ alkyl radical,
$R_2$ is a hydrogen atom, a halogen atom, a nitro radical, or a $C_1$ to $C_5$ alkyl radical,
n and m are equal to 0 or to 1, but not independently of the other, so that if n is equal to 1, then m is equal to 0 and if n is equal to 0, then m is equal to 1.

2. The method of claim 1 wherein said treatment is for functional and organic venous insufficiency.

3. The method of claim 1 wherein said treatment is for hemorrhoidal pathologies.

4. The method of claim 1 wherein said treatment is for migraines.

5. The method of claim 1 wherein said treatment is for osteoarticular, dermatological, and cardiovascular inflammations.

6. The method of claim 1 wherein said treatment is for shock caused by a significant drop in blood pressure.

7. The method of claim 6, wherein said shock is septic shock.

8. A composition of matter comprising 5,6-dihydro-5,6-dioxo-9-methyl-naptho[1',2':4,5]imidizo[1,2-a]pyridine.

9. A composition of matter comprising 5,6-dihydro-5,6-dioxo-10-methyl-naptho[1',2':4,5]imidazo[1,2-a]pyridine.

10. A composition of matter comprising 5,6-dihydro-5,6-dioxo-11-methyl-naptho[1',2':4,5]imidazo[1,2-a]pyridine.

11. A composition of matter comprising 11-chloro-5,6-dihydro-5,6-dioxo-naptho[1',2':4,5]imidazo[1,2-a]pyridine.

12. A composition of matter comprising 5,6-dihydro-5,6-dioxo-9-fluoro-naptho[1',2':4,5]imidazo[1,2-a]pyridine.

13. A composition of matter comprising 9-chloro-5,6-dihydro-5,6-dioxo-4-nitro-naptho[1',2':4,5]imidazo[1,2-a]pyridine.

14. A composition of matter comprising 2-chloro-6,11-dihydro-6,11-dioxo-7-nitro-naptho[2',3':4,5]imidazo[1,2-a]pyridine.

15. A composition of matter comprising 2-chloro-6,11-dihydro-6,11-dioxo-10-nitro-naptho[2',3':4,5]imidazo[1,2-a]pyridine.

16. A composition of matter comprising 6,11-dihydro-6,11-dioxo-2-methyl-naptho[2',3':4,5]imidazo[1,2-a]pyridine.

17. A composition of matter comprising 2-chloro-6,11-dihydro-6,11-dioxo-naptho[2',3':4,5]imidazo[1,2-a]pyridine.

18. A composition of matter comprising 4-chloro-6,11-dihydro-6,11-dioxo-naptho[2',3':4,5]imidazo[1,2-a]pyridine.

19. A composition of matter comprising 6,11-dihydro-6,11-dioxo-2-fluoro-naptho[2',3':4,5]imidazo[1,2-a]pyridine.

20. A composition of matter comprising 10-chloro-5,6-dihydro-5,6-dioxo-naptho[1',2':4,5]imidazo[1,2-a]pyridine.

21. A composition of matter comprising 4-chloro-5,6-dihydro-5,6-dioxo-naptho[1',2':4,5]imidazo[1,2-a]pyridine.

22. A composition of matter comprising 4-bromo-5,6-dihydro-5,6-dioxo-naptho[1',2':4,5]imidazo[1,2-a]pyridine.

23. A composition of matter comprising 5,6-dihydro-5,6-dioxo-2-nitro-naptho[1',2':4,5]imidazo[1,2-a]pyridine.

24. A composition of matter comprising 6,11-dihydro-6,11-dioxo-7-nitro-naptho[2',3':4,5]imidazo[1,2-a]pyridine.

25. A composition of matter comprising 6,11-dihydro-6,11-dioxo-10-nitro-naptho[2',3':4,5]imidazo[1,2-a]pyridine.

26. A composition of matter comprising 6,11-dihydro-6,11-dioxo-8-fluoro-naptho[2',3':4,5]imidazo[1,2-a]pyridine.

27. A composition of matter comprising 6,11-dihydro-6,11-dioxo-9-fluoro-naptho[2',3':4,5]imidazo[1,2-a]pyridine.

28. A composition of matter comprising 5,6-dihydro-5,6-dioxo-2-fluoro-naptho[1',2':4,5]imidazo[1,2-a]pyridine.

29. A composition of matter comprising 5,6-dihydro-5,6-dioxo-3-fluoro-naptho[1',2':4,5]imidazo[1,2-a]pyridine.

30. A composition of matter comprising 6,11-dihydro-6,11-dioxo-7-fluoro-naptho[2',3':4,5]imidazo[1,2-a]pyridine.

31. A composition of matter comprising 6,11-dihydro-6,11-dioxo-10-fluoro-naptho[2',3':4,5]imidazo[1,2-a]pyridine.

32. A composition of matter comprising 5,6-dihydro-5,6-dioxo-1-fluoro-naptho[1',2':4,5]imidazo[1,2-a]pyridine.

33. A composition of matter comprising 5,6-dihydro-5,6-dioxo-4-fluoro-naptho[1',2':4,5]imidazo[1,2-a]pyridine.

34. A composition of matter comprising 4,9-dichloro-5,6-dihydro-5,6-dioxo-naptho[1',2':4,5]imidazo[1,2-a]pyridine.

35. A composition of matter comprising 6,11-dihydro-6,11-dioxo-7-methyl-naptho[2',3':4,5]imidazo[1,2-a]pyridine.

36. A composition of matter comprising 6,11-dihydro-6,11-dioxo-10-methyl-naptho[2',3':4,5]imidazo[1,2-a]pyridine.

37. A composition of matter comprising 5,6-dihydro-5,6-dioxo-1-methyl-naptho[1',2':4,5]imidazo[1,2-a]pyridine.

38. A composition of matter comprising 5,6-dihydro-5,6-dioxo-4-methyl-naptho[1',2':4,5]imidazo[1,2-a]pyridine.

39. A composition of matter comprising 2-chloro-6,11-dihydro-6,11-dioxo-7-methyl-naptho[2',3':4,5]imidazo[1,2-a]pyridine.

40. A composition of matter comprising 2-chloro-6,11-dihydro-6,11-dioxo-10-methyl-naptho[2',3':4,5]imidazo[1,2-a]pyridine.

41. A composition of matter comprising 9-chloro-5,6-dihydro-5,6-dioxo-1-methyl-naptho[1',2':4,5]imidazo[1,2-a]pyridine.

42. A composition of matter comprising 9-chloro-5,6-dihydro-5,6-dioxo-4-methyl-naptho[1',2':4,5]imidazo[1,2-a]pyridine.

43. A composition of matter comprising 6,11-dihydro-6,11-dioxo-8-methyl-naptho[2',3':4,5]imidazo[1,2-a]pyridine.

44. A composition of matter comprising 6,11-dihydro-6,11-dioxo-9-methyl-naptho[2',3':4,5]imidazo[1,2-a]pyridine.

45. A composition of matter comprising 5,6-dihydro-5,6-dioxo-2-methyl-naptho[1',2':4,5]imidazo[1,2-a]pyridine.

46. A composition of matter comprising 5,6-dihydro-5,6-dioxo-3-methyl-naptho[1',2':4,5]imidazo[1,2-a]pyridine.

47. A composition of matter comprising 2,3-dibromo-1,4-dihydro-1,4-dioxo-5-fluoronapthalene.

48. A composition of matter comprising 2,3-dibromo-1,4-dihydro-1,4-dioxo-6-fluoronapthalene.

49. A composition of matter comprising 2,3-dibromo-1,4-dihydro-1,4-dioxo-5-methylnapthalene.

\* \* \* \* \*